(12) United States Patent
Jensen et al.

(10) Patent No.: US 6,566,494 B1
(45) Date of Patent: May 20, 2003

(54) SUPPORT MATERIAL FOR SOLID PHASE ORGANIC SYNTHESIS

(75) Inventors: Knud J. Jensen, Minneapolis, MN (US); George Barany, Falcon Heights, MN (US); Micheal F. Songster, St. Paul, MN (US); Fernando Albericio, Barcelona (ES); Jordi Alsina, Barcelona (ES); Josef Vágner, Værløse (DE)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 09/309,828

(22) Filed: May 11, 1999

Related U.S. Application Data

(62) Division of application No. 08/665,509, filed on Jun. 18, 1996, now Pat. No. 5,917,015.

(51) Int. Cl.$^7$ .................................................. C07K 1/04

(52) U.S. Cl. ........................................................ 530/334

(58) Field of Search ........................................ 530/334

(56) References Cited

U.S. PATENT DOCUMENTS

| | | | | |
|---|---|---|---|---|
| 4,062,746 A | | 12/1977 | Rich et al. ............. | 204/159.12 |
| 4,108,846 A | | 8/1978 | Meienhofer .......... | 260/112.5 R |
| 4,732,956 A | * | 3/1988 | Woods .................. | 526/260 |
| 5,117,009 A | | 5/1992 | Barany ................. | 549/394 |
| 5,176,983 A | * | 1/1993 | Horn .................... | 430/270 |
| 5,196,566 A | | 3/1993 | Barany et al. ........ | 560/61 |
| 5,235,028 A | | 8/1993 | Barany et al. ........ | 528/335 |
| 5,306,562 A | | 4/1994 | Barany ................. | 428/402 |
| 5,861,532 A | * | 1/1999 | Brown .................. | 564/12 |
| 5,958,792 A | * | 9/1999 | Desai ................... | 436/518 |

OTHER PUBLICATIONS

J.G. Adamson et al., "Use of Marfey's Reagent to Quantitate Racemization upon Anchoring of Amino Acids to Solid Supports for Peptide Synthesis", *Analytical Biochemistry*, 202, 210–214 (1992).

F. Albericio et al., "Allyl–based orthogonal solid phase peptide synthesis", *Peptides*, Proceedings of the Twenty–Second European Peptide Symposium, Sep. 13–19, 191–193 (1992).

F. Albericio et al., "An Acid–labile anchoring linkage for solid–phase synthesis of C–terminal peptide amides under mild conditions", *Int. J. Peptide Protein Res.*, 30, 206–216 (1987).

F. Albericio et al., "Preparation and Application of the 5–(4–(9–Fluorenylmethyloxycarbonyl)amino methyl –3,5–dimethoxyphenoxy)– valeric Acid (PAL) Handle for the Solid–Phase Synthesis of C–Terminal Peptide Amides under Mild Conditions", *J. Org. Chem.*, 55, 3730–3743 (1990), plus Supplementary Materials (19 pages).

G. Barany et al., "A New Amino Protecting Group Removable by Reduction. Chemistry of the Dithiasuccinoyl (Dts) Function", *J. Amer. Chem. Soc.*, 99, 7363–7365 (1977).

G. Barany et al., "Novel polyethylene glycol–polystyrene (PEG–PS) graft supports for solid–phase peptide synthesis", *Peptides*, 267–268 (1992).

G. Barany et al., "Solid–Phase Peptide Synthesis", *The Peptides*, vol. 2, Title Page, Copyright Page, Table of Contents, pp. v–viii (1979).

G. Barany et al., "Solid–phase peptide synthesis: a silver anniversary report", *Int. J. Peptide Protein Res.*, 30, 705–739 (1987).

C. Boojamra et al., "An Expedient and High–Yielding Method for the Solid–Phase Synthesis of Diverse 1,4–Benzodiazepine–2,5–diones", *J. Org. Chem.*, 60, 5742–5743 (1995).

Cohn et al., "IUPAC–IUB Commission on Biochemical Nomenclature Symbols for Amino–Acid Derivatives and Peptides Recommendations", *J. Biological Chem.*, 247, 977–983 (1972).

C.G. Fields et al., "Edman Degradation Sequence Analysis of Resin–Bound Peptides Synthesized by 9–Fluorenylmethoxycarbonyl Chemistry", *Peptide Research*, 6, 39–47 (1993).

C.G. Fields et al., "HBTU Activation for Automated Fmoc Solid–Phase Peptide Synthesis", *Peptide Research*, 4, 95–101 (1991).

M. Mutter et al., "A Chemical Approach to Protein Design—Template–Assembled Synthetic Proteins (TASP)", *Angew. Chem. Int. Ed. Engl.*, 28, 535–554 (1989).

E. Nicolás et al., "A New Approach to the Solid–Phase Peptide Synthesis of Peptide Alkyl–Amides and Esters", *Tetrahedron Letters*, 33, 2183–2186 (1992).

"Program and Abstracts", *Fourteenth American Peptide Symposium, American Peptide Society*, Title Page, Table of Contents, (1–1 to 1–22), Columbus, OH, Jun. 18–23, 1995.

M. Renil et al., "Synthesis of fully Protected Peptides on a Tetraethyleneglycol Diacrylate (TTEGDA)–Crosslinked Polystyrene support with a photolytically Detachable 2–Nitrobenzyl Anchoring group", *Tetrahedron Letters*, 35, 3809–3812 (1994).

(List continued on next page.)

*Primary Examiner*—David Lukton
(74) *Attorney, Agent, or Firm*—Mueting, Raasch & Gebhardt, P.A.

(57) ABSTRACT

A support material for solid phase synthesis is provided having an amine-containing organic group attached to it through a linker. The support material is of the following general formula (Formula I):

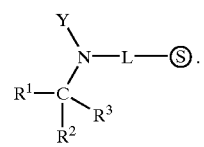

14 Claims, No Drawings

OTHER PUBLICATIONS

J. Rivier et al., "Anchoring of Amino Functions to Supports in Solid Phase Peptide Synthesis", *Peptides*, Proceedings of the 50th Anniversary Symposium, Szeged, Hungary, Aug. 31–Sep. 4, 1987, pp. 75–78.

Y. Sasaki et al., "Solid Phase Synthesis of Peptides Containing the $CH_2NH$ Peptide Bond Isostere", *Peptides*, 8, 119–121 (1987).

S. Sharma et al., "Reductive Amination with Tritylamine as an Ammonia Equivalent: Efficient Preparation of the 5–[4–[[(9–Fluorenylmethyloxycarbonyl)–amino]methyl]–3, 5–dimethoxyphenoxy]valeric Acid (PAL) Handle for Peptide Synthesis", *J. Org. Chem.*, 58, 4993–4996 (1993).

J. Tam et al., "Strong Acid Deprotection of Synthetic Peptides: Mechanisms and Methods", *The Peptides*, 9, Chapter 5, 185–248 (1987).

F. Weygand et al., "Leicht Abspaltbare Schutzgruppen Für Säureamidfunktionen" *Tetrahedron Letters*, 29, 3483–3487 (1966).

P. Williams et al., "Convergent Solid–Phase Peptide Synthesis", *Tetrahedron*, 49, 11065–11133 (1994).

G.B. Fields et al., "The Versatility of Solid Phase Peptide Synthesis", *Innovation and Perspectives in Solid Phase Synthesis*, R. Epton, Ed., Solid Phase Conference Coordination, Ltd., Birmingham, United Kingdon, 241–260 (1990).

J. Green, "Solid Phase Synthesis of Lavendustin A and Analogues", *J. Org. Chem.*, 60, 4287–4290 (1995).

F. Guibé et al., "Use of an Allylic Anchor Group and of its Palladium Catalyzed Hydrostannolytic Cleavage in the Solid Phase Synthesis of Protected Peptide Fragments", *Tetrahedron Ltrs.*, 30, 2641–2644 (Jun. 1989).

K.J. Jensen et al., "A Novel Handle Approach for Solid Phase Peptide Synthesis: Backbone Amide Linker (BAL) Anchoring", *Peptides: Chemistry, Strucure and Biology*, Chapter 6, 30–32, P.T.P. Kaumaya and R.S. Hodges, eds., (Aug. 1, 1996).

K.J. Jensen et al., "Backbone Amide (BAL) Anchoring in Solid–Phase Peptide Synthesis", *Fourth International Symposium on Solid Phase Synthesis*, 4 pps., Edinburgh, Scotland, UK, Sep. 12–16, 1995 (Abstract and Coverpage Only).

K.J. Jensen et al., "Backbone Amide (BAL) Anchoring in Solid–Phase Peptide Synthesis", *Innovation and Perspectives in Solid Phase Synthesis & Combinatorial Chemical Libraries: Biomedical & Applications*, 1996, 187–190, R. Epton, eds., Mayflower Scientific Ltd., Kingswinford, England (Apr. 28, 1997).

T. Johnson et al., "N,O–bisFmoc Derivatives of N–(2–Hydroxy–4–methoxybenxyl)–amino acids: Useful Intermediates in Peptide Synthesis", *J. Peptide Science*, 1, 11–25 (1995).

R.B. Merrifield, "Solid Phase Peptide Synthesis. I. The Synthesis of a Tetrapeptide", *J. Amer. Chem. Soc.*, 85, 2149–2154 (1963).

D. Mullen et al., "A New Fluoridolyzable Anchoring Linkage for Orthogonal Solid–Phase Peptide Synthesis: Design, Preparation, and Application of the N–(3 or 4)–[[4–(Hydroxymethyl)phenoxyl]–tert–butylphenylsilyl]phenyl Pentanedioic Acid Monoamide (Pbs) Handle", *J. Org. Chem.*, 53, 5240–5248 (1988).

* cited by examiner

SUPPORT MATERIAL FOR SOLID PHASE ORGANIC SYNTHESIS

This is a division of application Ser. No. 08/665,509, filed Jun. 18, 1996, now U.S. Pat. No. 5,917,015, which is incorporated herein by reference.

STATEMENT OF GOVERNMENT RIGHTS

The present invention was made with support from National Institutes of Health Grant No. GM 42722. The government may have certain rights in the invention.

BACKGROUND OF THE INVENTION

Solid-phase peptide synthesis (SPPS) involves a covalent attachment step (i.e., anchoring) that links the nascent peptide chain to an insoluble polymeric support (i.e., support material) containing appropriate functional groups for attachment. Subsequently, the anchored peptide is extended by a series of addition (deprotection/coupling) cycles that involve adding $N^\alpha$-protected and side-chain-protected amino acids stepwise in the C to N direction. Once chain assembly has been accomplished, protecting groups are removed and the peptide is cleaved from the support.

Typically, SPPS begins by using a handle to attach the initial amino acid residue to the functionalized polymeric support. A handle (i.e., linker) is a bifunctional spacer that, on one end, incorporates features of a smoothly cleavable protecting group, and on the other end, a functional group, often a carboxyl group, that can be activated to allow coupling to the functionalized polymeric support. Known handles include acid-labile p-alkoxybenzyl (PAB) handles, photolabile o-nitrobenzyl ester handles, and handles such as those described by Albericio et al., *J. Org. Chem.*, 55, 3730–3743 (1990) and references cited therein, and in U.S. Pat. No. 5,117,009 (Barany) and U.S. Pat. No. 5,196,566 (Barany et al.).

For example, if the support material is prepared with amino-functionalized monomers, typically, the appropriate handles are coupled quantitatively in a single step onto the amino-functionalized supports to provide a general starting point of well-defined structures for peptide chain assembly. The handle protecting group is removed and the C-terminal residue of the $N^\alpha$-protected first amino acid is coupled quantitatively to the handle. Once the handle is coupled to the solid-phase and the initial amino acid or peptide is attached to the handle, the general synthesis cycle proceeds. The synthesis cycle generally consists of deprotection of the $N^\alpha$-amino group of the amino acid or peptide on the resin, washing, and, if necessary, a neutralization step, followed by reaction with a carboxyl-activated form of the next $N^\alpha$-protected amino acid. The cycle is repeated to form the peptide or protein of interest. Solid-phase peptide synthesis methods using functionalized insoluble supports are well known. See, for example, Merrifield, *J. Am. Chem. Soc.*, 85, 2149 (1963); Barany and Merrifield, In *The Peptides, Vol. 2*, pp. 1–284 (1979); Gross, E. and Meienhofer, J., Eds., Academic: New York; and Barany et al., *Int. J. Peptide Protein Res.*, 30, 705–739 (1987).

Most current methods of SPPS rely on the a-carboxyl function of the eventual C-terminal amino acid residue to achieve anchoring to the support. However, this approach limits SPPS to the formation of peptides having acid, amide, or monosubstituted amide functionality, for example, as the C-terminal functionality, unless more complex procedures are used. Furthermore, certain functionalities, such as aldehydes, cannot typically be obtained using this approach. Cyclic peptides are also not possible using this method. Also, racemization of sensitive amino acid residues in the synthesis of peptide acids is a problem using this method.

Side-chain anchoring, i.e., methods of SPPS that use amino acids with side-chain functional groups for attachment of peptides, is potentially useful for the formation of unusual C-terminal functionalities as well as cyclic peptides. However, side-chain anchoring is inherently limited to certain trifunctional amino acids. Therefore, it would be desirable to develop a general method of SPPS that: (1) allows for the preparation of a wider variety of peptides; (2) does not typically result in racemization of sensitive amino acid residues; and (3) can incorporate a wider variety of amino acids into cyclic peptides.

SUMMARY OF THE INVENTION

The present invention provides a method of forming a support material linked to an amine-containing organic group for solid phase organic synthesis comprising:

(a) attaching a preformed divalent linker to a support material; and (b) attaching an amine-containing organic group to the preformed divalent linker;

wherein steps (a) and (b) are carried out to form a support material linked to an amine-containing organic group of the following formula (Formula I):

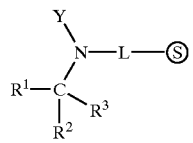

wherein:
(i) Ⓢ represents a support material;
(ii) L represents a divalent linker;
(iii) Y represents H or a protecting group; and
(iv) $R^1$, $R^2$, and $R^3$ are each independently H or an organic group.

A preferred divalent linker (L) is of the formula (Formula II):

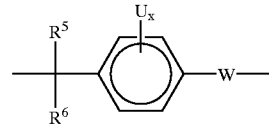

wherein:
each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, an alkylsulfonyl group, an alkylsulfoxide group, a halogeno group, and a nitro group, wherein any two U groups can be joined to form a ring; W is a functionalized spacer group for anchoring the linker to the support material; $R^5$ and $R^6$ are each independently H, an alkyl group, or an aryl group; and x=0–4.

To synthesize an organic compound, such as a peptide, once the support material of Formula I is prepared, a second organic group is attached to the N atom to build an organic compound. This is done using standard solid phase synthesis techniques and repeated addition cycles of deprotection and coupling.

The present invention also provides a method of synthesizing an organic compound comprising:

(a) providing an aldehyde-functionalized support material having the following formula (Formula III):

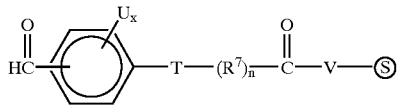

wherein:
(i) Ⓢ represents a support material;
(ii) V is NH, S or O;
(iii) T is O, NH, NHC(O)R$^4$, or S, wherein R$^4$ is an alkylene group, an arylene group, or an aralkylene group;
(iv) R$^7$ is an alkylene group, an arylene group, or an oxyalkylene group;
(v) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, an alkylsulfonyl group, an alkylsulfoxide group, a halogeno group, and a nitro group, wherein any two U groups can be joined to form a ring;
(vi) x=0–4; and
(vii) n=1–18;

(b) attaching an amine-containing organic group to the aldehyde functionality under reducing conditions; and (c) attaching a second organic group to the N atom of the amine-containing organic group to build an organic compound.

The aldehyde-functionalized support material of Formula III is also provided, along with a kit for synthesizing an organic compound. The kit includes an aldehyde-functionalized support material having the Formula III and instructions for preparing an organic compound on the aldehyde-functionalized support material.

The present invention also provides a support material linked to an amine-containing organic group for solid-phase synthesis of an organic compound, wherein the support material has the following formula (Formula I):

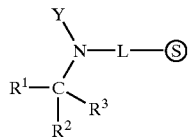

wherein:
(a) Ⓢ represents a support material;
(b) L represents a divalent linker;
(c) Y represents H or a protecting group;
(d) R$^1$ and R$^2$ are each independently H or an organic group; and
(e) R$^3$ is an organic group having a protecting group Z that is removable under mild conditions.

The present invention also provides a preformed linker having an amine-containing organic group attached thereto, of the formula (Formula IV):

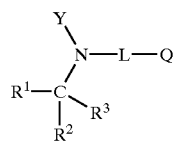

wherein:
(a) L represents a divalent linker;
(b) Q represents a group selected from the group consisting of C(O)OH, C(O)OPfp, C(O)F, C(O)Br, C(O)Cl, OH, Br, Cl;
(c) Y represents H or a protecting group;
(d) R$^1$ and R$^2$ are each independently H or an organic group; and
(e) R$^3$ is an organic group having a protecting group Z that is removable under mild conditions.

As used herein, the term "organic group" means a hydrocarbon group that is classified as an aliphatic group, cyclic group, or combination of aliphatic and cyclic groups (e.g., aralkyl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group. The term "heterocyclic group" means a closed ring hydrocarbon in which one or more of the atoms in the ring is an element other than carbon (e.g., nitrogen, oxygen, sulfur, etc.).

As is well understood in this technical area, a large degree of substitution is not only tolerated, but is often advisable. Substitution is anticipated on the materials of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

DETAILED DESCRIPTION OF THE INVENTION

The present invention provides a method for preparing organic compounds, particularly peptides, using solid-phase synthesis. The method involves anchoring an amine-containing organic group, which is the starting point for building the organic compound, to a support material using a divalent linker. Specifically, if peptides are being prepared, the amino acid residue or peptide is anchored through its backbone to the support material. This is in contrast to conventional methods of solid-phase peptide synthesis, for example, that involve anchoring the amine-containing organic group through a side-chain functional group of an amino acid residue, or through the a-carboxyl functionality of the eventual C-terminal amino acid residue.

This backbone amide linker (BAL) approach for the preparation of peptides avoids some of the aforementioned problems and allows for the preparation of peptides or other organic compounds having a variety of C-terminal functionalities, e.g., not only acids, but also thioacids and thioesters, alcohols, disubstituted amides, and aldehydes, among others. It also allows for the preparation of cyclic peptides using a wider variety of amino acids. Also, this approach is advantageous because there is little racemization of sensitive amino acid residues at room temperature.

The support material linked to an amine-containing organic group has the following general formula (Formula I):

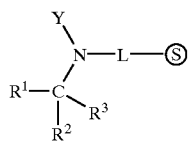

wherein:
  Ⓢ represents a support material, typically a solid support, which may include a variety of functional groups for attachment, and may or may not include a spacer; L represents a divalent linker; Y represents H or a protecting group, such as an $N^\alpha$-amine protecting group; and $R^1$, $R^2$, and $R^3$ are each independently H or an organic group.

The support material of Formula I is prepared by attaching a preformed divalent linker to a support material, and attaching an amine-containing organic group to the preformed divalent linker. These two steps can be carried out in either order. That is, the amine-containing organic group can be attached to the preformed divalent linker prior to attaching the preformed divalent linker to the support material. Alternatively, the preformed divalent linker can be attached to the support material prior to attaching the amine-containing organic group to the preformed divalent linker.

As used herein, a preformed divalent linker (i.e., handle) is one that is prepared and then added to the support material as opposed to being formed or built up on the support material. Although all support materials with linkers attached thereto described herein are not made using preformed handles, it is particularly desirable to do so. Thus, the methods of the present invention attach a preformed divalent linker to a support material either before or after it is attached to an amine-containing organic group.

Advantageously, in preferred embodiments, the method of preparing the support material of Formula I is carried out under relatively mild conditions. Preferably, the step of attaching the amine-containing organic group to the divalent linker, and more preferably both the step of attaching the amine-containing organic group to the divalent linker and the step of attaching the divalent linker to the support material, is carried out at a temperature of no greater than 35° C. This reduces the chances of racemization of any chiral groups, such as chiral amino acid residues. The temperature at which either or both of these steps is carried out is more preferably about 0–30° C., and most preferably about 20–25° C. Typically, either or both of these steps is carried out for no greater than about 30 hours each, preferably for no greater than about 10 hours, more preferably for no greater than about 5 hours, and most preferably for no greater than about 2 hours each.

In the amine-containing organic group (i.e., —N(Y)—C($R^1$)($R^2$)($R^3$)), the groups $R^1$, $R^2$, and $R^3$ are each independently H or an organic group. They can be a wide variety of organic groups, such as alkyls, aryls, heterocyclics, etc. Typically, at least one of $R^1$, $R^2$, and $R^3$ is an amino acid side chain, which can be proteinogenic or non-proteinogenic amino acid side-chains.

Preferably, $R^1$, $R^2$, and $R^3$ are each independently H or a ($C_1$–$C_{18}$)alkyl group, a ($C_6$–$C_8$)aryl group, a ($C_1$–$C_{18}$)alk($C_6$–$C_{18}$)aryl group, a ($C_5$–$C_{18}$)heterocyclic group, or a ($C_1$–$C_{18}$)alk($C_3$–$C_{18}$)heterocyclic group. More preferably, at least one of $R^1$, $R^2$, and $R^3$ is selected from the group consisting of a —$CH_3$, —$CH(CH_3)_2$, —$CH(CH_3)(CH_2CH_3)$, —$CH_2$—$CH(CH_3)_2$, —$(CH_2)_nX$ (n=1–4), and —$CH(CH_3)X$ group wherein X is selected from the group consisting of —OH, —$OCH_3$, —$NO_2$, —$NH_2$, —SH, —$SCH_3$, —C(O)OH, —C(O)$NH_2$, —$C_6H_5$, —$C6H_4OH$, indoyl, imidazoyl, and protected derivatives thereof.

For certain embodiments of the support material of Formula I, $R^1$ and $R^2$ are each independently H or an organic group as defined above, and $R^3$ is an organic group having a protecting group Z that is removable under mild conditions (e.g., moderate or weak acid, moderate or weak base, photolysis, thiolysis, palladium-catalyzed or rhodium-catalyzed nucleophilic transfer, hydrogenation, or fluoridolysis). As used herein, moderate or weak acids are those with an $H_O$ of −5 or higher, as defined by J. P. Tam et al., in The Peptides, Vol. 9 (S. Udenfriend and J. Meienhofer, Eds.), pp. 185–248, Academic Press, New York (1987). Examples of such acids include, but are not limited to, hydrochloric, acetic, dilute sulfuric, and trifluoroacetic acid. Moderate or weak bases are those having conjugate acids with a pka of of 15.0 or less. Examples of such bases include, but are not limited to, piperdine, morpholine, and 1,8-diazabicyclo[5.4.0]undec-7-ene.

Suitable protecting groups Z depend on the functionality of $R^3$, which could include amines, carbonyls, hydroxyls, carboxylic acids, aldehydes, thiocarbonyls, etc. In preferred embodiments of the support material of Formula I, $R^3$ is selected from the group consisting of —C(O)OZ, —C(O)SZ, —C(S)OZ, —C(OZ)$_2$$R^4$ (wherein $R^4$ is an alkyl group, an aryl group, or an aralkyl group), and —C(OZ)$_2$H. Examples of suitable protecting groups Z include allyl, ($C_1$–$C_4$)alkyls, trityl, etc. Preferably, the protecting group Z is selected from the group consisting of methyl, t-butyl, and allyl moieties.

The protecting group Y of the support material of Formula I can be a wide variety of protecting groups that can be removed using conditions that do not cleave the N—L bond, do not remove the linker from the support material, and do not adversely affect the compound (e.g., the peptide) being formed on the support material. Thus, the linker L and the protecting group Y are preferably chosen such that they can be removed in an orthogonal fashion. An orthoganol protection scheme is defined as one which makes use of two or more independent classes of groups, each one removed through a different chemical mechanism, allowing them to be removed in any order and in the presence of all the other classes.

Suitable protecting groups (Y) include, for example, those that can be removed using a wide variety of known conditions. Preferably, the protecting group Y is chosen such that it can be removed using mild conditions such as moderate or weak acid, moderate or weak base, photolysis, thiolysis, palladium- or rhodium-catalyzed nucleophilic transfer, hydrogenation, and fluoridolysis.

Examples of suitable protecting groups (Y) include, but are not limited to: formyl; alkyl groups; aryl groups such as p-phenylbenzyl and 9-phenylfluorenyl; alkenyl groups; aralkyl groups; aralkenyl groups; alkylcarbonyl groups such as acetyl (Ac) and derivatives of acetyl such as acetoacetyl, mono-, di-, and tri-halogen substituted acetyl (e.g., chloroacetyl, trichloroacetyl, trifluoroacetyl, etc.), o-nitrophenoxyacetyl, and phenylacetyl; arylcarbonyl groups such as benzoyl and p-nitrobenzoyl; alkyloxycarbonyl groups such as methoxycarbonyl, ethoxycarbonyl, isobutoxycarbonyl, 1-adamantyloxycarbonyl, 1,1-dimethyl-2-cyanoethoxycarbonyl, 1,1-dimethyl-2,2-dibromoethoxycarbonyl, 1,1-dimethyl-2,2,2-trichloroethoxycarbonyl, diisopropylmethoxycarbonyl, 2-iodoethoxycarbonyl, and 2-(trimethylsilyl)ethoxycarbonyl; aryloxycarbonyl groups such as m-nitrophenyloxycarbonyl and phenyloxycarbonyl; alkenylmethoxycarbonyl groups such as allyloxycarbonyl and 4-nitrocinnamyloxycarbonyl; alkenyloxycarbonyl groups such as vinyloxycarbonyl; aralkyloxycarbonyl groups such as 1-methyl-1-phenylethoxycarbonyl, 1-methyl-1-(4-pyridyl)ethoxycarbonyl, di(2-pyridyl)methoxycarbonyl, 1-methyl-1-(4-biphenyl)ethoxycarbonyl, and 9-fluorenylmethoxycarbonyl; cycloalkyloxycarbonyl groups such as cyclobutyloxycarbonyl, cyclohexyloxycarbonyl, cyclopentyloxycarbonyl, and 1-methyl-1-cyclohexyloxycarbonyl; alkylaminooxycarbonyl groups such as N-hydroxypiperidinyloxycarbonyl; sulfenyl groups such as o-nitrophenylsulfenyl and 3-nitropyridinesulfenyl; and sulfonyl groups such as p-toluenesulfonyl and β-(trimethylsilyl)ethanesulfonyl.

The protecting group Y is preferably an $N^\alpha$-amine protecting group. Examples of suitable $N^\alpha$-amine protecting groups include, for example, Fmoc, Aloc, Boc, Ddz, Npys, Nvoc, Bpoc, Teoc, Trt, SES, allyl, and t-Bu. These abbreviations are defined in the Examples section below. A preferred group of $N^\alpha$-amine protecting groups include, Fmoc, Aloc, and Boc.

The linker L in the support material of Formula I can be a wide variety of handles used in solid phase peptide synthesis. The linker L is a bifunctional spacer that, on one end, incorporates features of a smoothly cleavable protecting group, and on the other end, a functional group, often a carboxyl group, that can be activated to allow coupling to the functionalized support material. The linker can be a preformed linker or handle or it can be prepared on the support material. Suitable linker (L) examples include the PAL handle [5-(4'-aminomethyl-3',5'-dimethoxyphenoxy)valeric acid] and the XAL handle [5-(9-aminoxanthen-2-oxy)valeric acid]. Other suitable linkers include handles such as 4-(α-aminobenzyl)phenoxyacetic acid, 4-(α-amino-4'-methoxybenzyl)phenoxybutyric acid, 4-(α-amino-4'-methoxybenzyl)-2-methylphenoxyacetic acid, 2-hydroxyethylsulfonylacetic acid, 2-(4-carboxyphenylsulfonyl)ethanol, and those disclosed in G. B. Fields et al., *Synthetic Peptides: A User's Guide*, 1990, 77–183, G. A. Grant, Ed., W. H. Freeman and Co., New York.

A preferred group of linkers is of the following formula (Formula II):

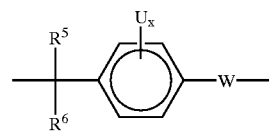

wherein:
each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, an alkylsulfonyl group, an alkylsulfoxide group, a halogeno group, and a nitro group, wherein any two U groups can be joined to form a ring; W is a functionalized spacer group for anchoring the linker to the support material; $R^5$ and $R^6$ are each independently H, an alkyl group, or an aryl group; and x=0–4.

Preferably, W is selected from the group consisting of $-(CH_2)_nC(O)NH-$, $-O(CH_2)_nC(O)NH-$, $-NH(CH_2)_nC(O)NH-$, $-OC(O)(CH_2)_nC(O)NH-$, $-C(O)(CH_2)_nC(O)NH-$, $-C(O)O(CH_2)_nC(O)NH-$, $-NHC(O)(CH_2)_nC(O)NH-$, $-O(CH_2)_nC_6H_4C(O)NH-$, $-C(O)O(CH_2)_nC_6H_4C(O)NH-$, $-OC(O)C_6H_4C(O)NH-$, $-OC(O)(CH_2CH_2O)_nC(O)NH-$, $-O(CH_2CH_2O)_nC(O)NH-$, $-NH(CH_2CH_2O)_nC(O)NH-$, and $-NHC(O)(CH_2CH_2O)_nC(O)NH-$ wherein n=1–18.

The present invention also provides a useful method of synthesizing an organic compound using an aldehyde-functionalized support material. This aldehyde-functionalized support material has the following formula (Formula III):

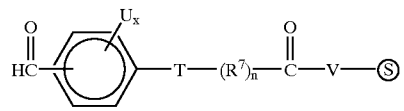

wherein:
Ⓢ represents a support material; V is NH, S or O; T is O, NH, NHC(O)$R^4$, or S, wherein $R^4$ is is an alkylene group, an arylene group, or an aralkylene group; $R^7$ is an alkylene group, an arylene group, or an oxyalkylene group; each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, an alkylsulfonyl group, an alkylsulfoxide group, a halogeno group, and a nitro group, wherein any two U groups can be joined to form a ring; x=0–4; and n=1–18. Preferably, $R^1$ is an alkylene group and n=1–4.

An amine-containing organic group is then typically attached to the aldehyde functionality under reducing conditions. Typically, this is carried out at a temperature of no greater than 35° C. for no greater than about 10 hours. As used herein, reducing conditions include NaBH$_3$CN, NABH$_4$, cat.H$_2$, and NaBH(OAc)$_3$. A second organic group, which may be a protected amino acid, is then attached to the N atom of the amine-containing group to build an organic compound. This is typically carried out in a nonprotic solvent selected from the group consisting of CH$_2$Cl$_2$, ClCH$_2$CH$_2$Cl, tetrahydrofuran, CH$_3$CN, toluene, pyridine, dioxane, diethyl ether, and benzene. The organic compounds prepared may or may not be a peptide, which may or may not be cyclic, or have a broad range of functional groups on the peptide being formed. For example, the method of the present invention can provide a terminal carboxylic acid group, ester group, aldehyde group, thioacid group, and thioester group.

The present invention also provides a kit that includes the aldehyde-functionalized support material of Formula III and instructions for preparing an organic compound on the aldehyde-functionalized support material.

The present invention also provides a preformed linker having an amine-containing organic group attached thereto, of the formula (Formula IV):

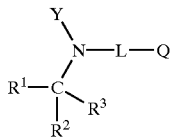

wherein:

L represents a divalent linker; Q represents a group selected from the group consisting of C(O)OH, C(O)OPfp, C(O)F, C(O)Br, C(O)Cl, OH, Br, Cl; Y represents H or a protecting group; R$^1$ and R$^2$ are each independently H or an organic group; and R$^3$ is an organic group having a protecting group Z that is removable under mild conditions.

The linker is attached to functionalized support materials or to spacer arms attached to the support materials. Typically, the support material includes hydroxyl, carboxyl, or amino functional groups, although other functional groups such as thiol, halogens, and silyl are possible. The support material can also include a spacer. Typically, a spacer is an alkyl chain (preferably a (C$_1$–C$_{20}$)alkyl chain) substituted with an amino group and a carboxyl group.

A variety of functionalized support materials can be used. They can be of inorganic or organic materials and can be in a variety of forms (e.g., membranes, particles, spherical beads, fibers, gels, glasses, etc.). Examples include, porous glass, silica, polystyrene, polydimethylacrylamides, cotton, paper, and the like. Examples of suitable support materials are described by G. B. Fields et al., Int. J. Peptide Protein Res., 1990, 35, 161–214 and G. B. Fields et al., Synthetic Peptides: A User's Guide, 1990, 77–183, G. A. Grant, Ed., W. H. Freeman and Co., New York. Functionalized polystyrene, such as amino-functionalized polystyrene, aminomethyl polystyrene, aminoacyl polystyrene, p-methylbenzhydrylamine polystyrene, or polyethylene glycol-polystyrene resins can be used for this purpose. Polyethylene glycol-polystyrene (PEG-PS) graft copolymers functionalized with amino groups are particularly useful support materials. Suitable PEG-PS resins are available from PerSeptive BioSystems (Framingham, Mass.) and are described in U.S. Pat. No. 5,235,028 (Barany et al.).

The support materials of the present invention can be prepared by attaching the linker to the support material and then attaching the amine-containing organic group, e.g., amino acid or peptide. The attachment reaction of the linker to the support material can be carried out using standard coupling methods, e.g., acylations or alkylations, as disclosed in, for example, F. Albericio et al., J. Org. Chem., 1990, 55, 3730–3743, or alkylations. For example, acylations promoted by N,N'-dicyclohexylcarbodiimide (DCC), or N,N'-diisopropylcarbodiimide (DIPCDI) plus 1-hydroxybenzotriazole (HOBt), or benzotriazoylyl-N-oxytris(dimethylamino)phosphonium hexafluorophosphate (BOP) plus 1-hydroxybenzotriazole (HOBt). Typically, one equivalent of the linker is used for each equivalent of functional group, e.g., amino group, present on the support. After attaching the amine-containing group to the linker, the protecting group can be added.

Alternatively, the linker, amino acid, and protecting group (if used) can be combined to form an optionally protected amino acid preformed linker, which is then attached to the support material. For example, in one embodiment of the present invention, an aldehyde precursor of the PAL handle [5-(4'-aminomethyl-3',5'-dimethoxyphenoxy)valeric acid], which is disclosed in Albericio and Barany, Int. J. Pept. Protein Res., 1987, 30, 206–216, can be coupled through a reductive amination procedure to the α-amine of the prospective C-terminal amino acid or other amine-containing compound, which can be protected as a tert-butyl, methyl, trityl, or allyl ester, or modified to a dimethyl acetal. The resultant intermediates, all secondary amines, can be treated with Fmoc-Cl or Fmoc-OSu to give the corresponding protected amino acid (or other amine-containing compound) preformed handles in 40–70% yields.

The invention will be further described by reference to the following detailed examples. These examples are offered to further illustrate the various specific and illustrative embodiments and techniques. It should be understood, however, that many variations and modifications may be made while remaining within the scope of the present invention.

EXAMPLES

General Procedures. Protected Fmoc- and Boc-amino acid derivatives, Fmoc-OSu, Fmoc-Cl, HATU, PyAOP, BOP, and HOAt were from the Biosearch Division of PerSeptive Biosystems (Framingham, Mass.), Bachem Bioscience (Philadelphia, Pa.) or Advanced ChemTech (Louisville, Ky.). MBHA resins for peptide synthesis were from Nova-Biochem (San Diego, Calif.). PEG-PS resins (with Nle "internal reference" amino acid) were from the Biosearch Division of PerSeptive BioSystems. Amino acid esters (glycine methyl ester, hydrochloride salt; phenylalanine methyl ester, hydrochloride salt; alanine tert-butyl ester, hydrochloride salt; leucine tert-butyl ester, hydrochloride salt) were from Advanced ChemTech or Bachem Bioscience. Piperidine, TFA, DIEA, HOBt, DMF, NaHCO$_3$, MgSO$_4$ (anhydrous), Na$_2$SO$_4$ (anhydrous), diethyl ether (HPLC grade), and 3 Å molecular sieves were from Fisher (Pittsburgh, Pa.). DIPCDI, diethyldithiocarbamic acid (sodium salt), allyl bromide, 2,2-dimethoxyethylamine, 2,4-dihydroxybenzaldehyde, 4-formyl-2,6-dimethylphenol, ethyl 5-bromovalerate, and sodium cyanoborohydride were from Aldrich (Milwaukee, Wis.). Methanol (anhydrous), dioxane, ethyl acetate (anhydrous), acetic anhydride, and hexane (HPLC grade) were from EM Science (Gibbstown, N.J.). CsHCO$_3$ was from Alfa (Ward Hill, Mass.). 5-(4-Formyl-3,5-dimethoxyphenoxy)valeric acid (PALdehyde) and 5-(2-formyl-3,5-dimethoxyphenoxy)valeric acid were prepared according to Albericio et al., J. Org. Chem., 1990, 55, 3730–3743. A mixture of 5-(4-formyl-3,5-dimethoxyphenoxy)butyric acid and 5-(2-formyl-3,5-dimethoxyphenoxy)butyric acid (o,p-PALdehyde), prepared essentially as described by Albericio and Barany, *Int. J. Pept. Protein Res.*, 1987, 30, 206–216, was provided by the Biosearch Division of PerSeptive BioSystems. Organic solvent extracts were dried over anhydrous $MgSO_4$ or $Na_2SO_4$, followed by solvent removal at reduced pressures and <40° C. Silica gel chromatography was performed with Silica Gel 60 (230–400 mesh) from EM Science, unless otherwise stated. Elemental analyses were conducted by M-H-W Laboratories (Phoenix, Ariz.). Melting points were determined on a Büichi apparatus and are uncorrected.

Thin-layer chromatography was performed on either Polygram SIL G/$UV_{254}$ plates (250 mm, 40×80 mm, Macherey-Nagel) or Kieselgel 60 $F_{254}$ (0.2 mm, 40×80 mm, EM Science). Spots were visualized by UV. Analytical HPLC was performed using a Waters (Milford, Mass.) Nova Pak analytical C-18 reversed phase-column (0.39×15 cm) Nucleosil (Macherey-Nagel) C-18 column (0.46×25 cm) on a Waters system configured with a 600E System Controller, a 625 Pump, a 700 Satellite WISP autoinjector, and a 996 Photodiode Array Detector or a Vydac (Hesperia, Calif.) analytical C-18 reversed phase-column (0.46×25 cm) on a Beckman System configured with two 112 pumps and a 165 Variable Wavelength Detector. Low resolution fast atom bombardment mass spectroscopy (FABMS) was carried out in glycerol-$H_2O$ or 3-nitrobenzyl alcohol (MNBA) matrices on a VG Analytical 7070E-HF low-resolution double-focusing mass spectrometer equipped with a VG 11/250 data system, operated at a resolution of 2000. Electrospray mass spectrometry was performed on a Perkin Elmer Sciex API III triple quadrupole mass spectrometer equipped with an ionspray interface. Parameters were: ionspray voltage 5000V, interface temperature 55° C., potential on first quadrupole 30V, orifice voltage varied from 50 to 150V. The curtain gas flow ($N_2$) and the nebulizer gas (ultrapure air) were set at 0.8–1.0 L/minutes. Molecular masses were calculated with the Sciex MacSpec 3.22 programm. MALDI-TOF mass spectrometry was performed on a Kompact Maldi I (Kratos Analytical). $^1H$ NMR spectroscopy was performed on Varian VXR 300 and VXR 500 instruments operating at 300 and 500 MHz, respectively. Chemical shifts (δ) are expressed in parts per million downfield from TMS. Coupling constants, in parentheses, are expressed in hertz. Amino acid analyses were carried out on a Beckman 6300 analyzer. Samples were hydrolyzed with 6 N HCl in propionic acid at 160° C., for 1 hour (condition A), or with an added 1 drop of phenol at 155° C., for 3 hours (condition B). Reported cleavage yields are based on amino acid ratios with respect to Ile "internal reference" amino acid of recovered peptidyl-resins after TFA treatment.

Example 1

$N^\alpha$-[4-(carboxylbutyloxy)-2,6-dimethoxybenzyl]-$N^\alpha$-(9-fluorenylmethoxycarbonyl)glycine methyl ester

5-(4-Formyl-3,5-dimethoxyphenoxy)valeric acid (140 mg, mw 282.3, 0.5 mmol), glycine methyl ester, hydrochloride salt, (63 mg, mw 125.6, 0.5 mmol) and $NaBH_3CN$ (31 mg, mw 62.84, 0.5 mmol) were combined in a 50 mL round-bottom flask and suspended in methanol (8 mL) and stirred at 25° C. for 60 minutes. The suspension was concentrated to dryness in vacuo and the remaining oil was resuspended in dioxane-water (1:1, 4 mL). Solid $NaHCO_3$ (126 mg, mw 84.0, 1.5 mmol) was added and the suspension was cooled in an ice-bath. Fmoc-OSu (253 mg, mw 337.3, 0.75 mmol) dissolved in dioxane (2 mL) was added to the suspension. Stirring was continued for 1 hour while cooling in an ice-bath, and at 25° C. overnight. The pH was then adjusted to 9 by addition of saturated aqueous $NaHCO_3$. The suspension was diluted with water (20 mL) and washed with diethyl ether (2×25 mL). The phase separations were slow and the ether layer remained cloudy. The aqueous layer was acidified to pH 3 with 4 N aqueous HCl and extracted with ethyl acetate (3×30 mL). The combined organic phases were dried over $MgSO_4$, filtered and concentrated to dryness in vacuo to provide an oil (278 mg, 96%).

$^1H$ NMR (500 MHz, DMSO-$d_6$, 368 K) δ11.61 (broad s), 7.85 (d, J=6.9; 2H), 7.7–7.5, m; 2H), 7.40 (t, J=7.4; 2H), 7.32 (m; 2H), 6.22 (s; 2H), 4.48 (broad s; 1H), 4.36 (d, J=6.7; 2H), 4.32 (dd, J=10.8, 6.9; 1H), 4.26 (broad s; 1H), 4.01 (t, J=6.2; 2H), 3.78–3.72 (m; 2H), 3.70 (s; 6H), 3.68 (s; 1H), 3.64 (s; 1H), 3.59 (s; 3H), 3.58 (s; 1H), 2.60 (s; 1H), 2.29 (t, J=7.1; 2H), 1.75 (q, J=13.7, 6.5; 2H), 1.70 (q, J=14.2, 7.4; 2H).

FABMS m/z calcd for $C_{32}H_{35}NO_9$: 577.6, found: 577.5 [$M^+$.].

Example 2

$N^\alpha$-[4-(carboxylbutyloxy)-2,6-dimetboxybenzyl]-$N^\alpha$-(9-fluorenylmethoxycarbonyl)glycine allyl ester

Preparation of H-Gly-OAl trifluoroacetate salt: $N^\alpha$-Boc-Gly-OH (8.76 g, mw 175.2, 50 mmol) was suspended in water-dioxane (1:4, 100 mL). $CsHCO_3$ (10.7 g, mw 193.92, 55 mmnol), dissolved in water (20 mL) was added over 5 minutes; 10 minutes later the suspension was concentrated to dryness in vacuo. The remaining foam was suspended in DMF (80 mL), stirred with allyl bromide (4.8 mL, mw 121.0, ρ 1.40, 55 mmol) at 25° C. for 14 hours, and then concentrated to dryness in vacuo. The solid was suspended in ethyl acetate (300 mL) and extracted with 10% aqueous $NaHCO_3$ (3×150 mL). The aqueous phase was backwashed with ethyl acetate (100 mL) and the combined organic phases were dried over $MgSO_4$, filtered, and concentrated in vacuo to an oil; Yield 10.6 g. The crude product was purified by vacuum liquid chromatography (over TLC grade silica gel 60 G using ethyl acetate-hexane [1:4] as eluent); Yield 9.3 g. The oil was treated with TFA-$CH_2Cl_2$ (1:1, 50 mL) for 1 hour and then concentrated in vacuo to an oil, which was washed with diethyl ether (3×50 mL) to give off-white crystals (7.74 g, 68%).

Preparation of $N^\alpha$-[4-(carboxylbutyloxy)-2,6-dimethoxybenyl]-$N^\alpha$-(9-fluorenylmethoxycarbonyl)glycine allyl ester: 5-(4-Formyl-3,5-dimethoxyphenoxy)valeric acid (140 mg, mw 282.3, 0.50 mmol) and glycine allyl ester, trifluoroacetate salt, (138 mg, mw 229.2, 0.6 mmol) were dissolved in methanol (5 mL) in a 25 mL round-bottom flask, and stirred at 25° C. for 10 minutes. $NaBH_3CN$ (47 mg, mw 62.84, 0.75 mmol) was added and the suspension stirred at 25° C. for 60 minutes. The suspension was concentrated to dryness in vacuo and the remaining oil was resuspended in dioxane-saturated aqueous $NaHCO_3$ (2:1, 15 mL) and the suspension was cooled in an ice-bath. Fmoc-OSu (223 mg, mw 337.3, 0.66 mmol) was dissolved in dioxane (2 mL) and added to the suspension. Stirring was continued for 1 hour while cooling in an ice-bath at 5° C. for 14 hours, and then at 25° C. for 2 hours. The suspension was diluted with water (20 mL) and washed with diethyl ether (2×25 mL). The aqueous layer was acidified to pH 3 by addition of 0.5 N aqueous HCl and extracted with ethyl acetate (3×20 mL). The combined organic phases were dried over $MgSO_4$, filtered and concentrated to dryness in vacation to provide an oil (286 mg, 95%).

¹H NMR (500 MHz DMSO-d₆, 294 K) δ12.05 (broad s), 10.48 (broad s), 7.87 (d, J=7.3; 3H), 7.76 (t, J=6.1; 1H), 7.68 (t, J=7.3; 2H), 7.40 (t, J=7.3; 3H), 7.31 (t, J=7.5; 3H), 6.19 (broad s, 1H), 5.87 (m; 1H), 5.29 (d, J=17.1; 1H), 5.19 (d, J=10.7; 1H), 4.57 (d, J=4.5; 2H), 4.28 (m; 2H), 4.22 (t, J=6.8; 1H), 3.8–3.1 (m; ~20H), 2.17 (broad s; 2H), 1.49 (broad s, 4H).

FABMS m/z calcd for $C_{34}H_{37}NO_9$: 603.25, found: 603.2 [M⁺.].

Example 3

N$^\alpha$-[4-(carboxylbutyloxy)-2,6-dimethoxybenzyl]-N$^\alpha$-(9-fluorenylmethoxycarbonyl)phenylalanine methyl ester 5-(4-Formyl-3,5-dimethoxyphenoxy)valeric acid (560 mg, mw 282.3, 2.0 mmol), phenylalanine methyl ester, hydrochloride salt, (431 mg, mw 215.7, 2.0 mmol) and NaBH₃CN (189 mg, mw 62.8, 3.0 mmol) were suspended in methanol (6 mL) in a 25 mL round-bottom flask and stirred at 25° C. for 60 minutes. The suspension was concentrated to dryness in vacuo and the remaining oil was resuspended in dioxane-water (1:1, 12 mL). Solid NaHCO₃ (504 mg, mw 84.01, 6 mmol) was added and the suspension cooled in an ice-bath. Fmoc-Cl (569 mg, mw 258.7, 2.2 mmol) was dissolved in dioxane (4 mL) and added to the suspension. Stirring was continued for 1 hour while cooling on an ice-bath, and then at 25° C. for 26 hours. The suspension was diluted with water (50 mL) and washed with hexane (2×50 mL). The phase separations were slow and the hexane layer remained cloudy. The aqueous layer was acidified to pH 3 by addition 0.5 N aqueous HCl (3 mL) and extracted with ethyl acetate (3×50 mL). The first separation was left for 2 hours, the second overnight. The combined organic phases were dried over MgSO₄, filtered and concentrated to dryness in vacuo to provide an oil (1.14 g, 84%).

¹H NMR (500 MHz, DMSO-d₆, 368 K) δ11.33 (broad s), 7.84 (d, J=7.0; 2H), 7.66 (t, J=9.5, 7.5; 2H), 7.39 (q, J=14.0, 7.0; 2H), 7.32 (t, J=7.3; 2H), 7.09 (broad s, 3H), 6.78 (broad s, 2H), 6.10 (s, 2H), 4.45 (dd, J=10.0, 5,8; 1H), 4.30 (m; 1H), 4.26 (t, J=6.0; 2H), 4.16 (d, J=14.6; 1H), 3.98 (t, J=6.5; 2H), 3.87 (broad s, 1H), 3.61 (s, 6H), 3.41 (broad s, 3H), 2.28 (t, J=7.3; 2H), 1.74 (m, 2H), 1.69 (m, 2H).

FABMS m/z calcd for $C_{39}H_{41}NO_9$: 667.28, found: 667.3 [M⁺.].

Example 4

N$^\alpha$-[4-(carboxylbutyloxy)-2,6-dimethoxybenzyl]-N$^\alpha$-(9-fluorenylmethoxycarbonyl)alanine tert-butyl ester 5-(4-Formyl-3,5-dimethoxyphenoxy)valeric acid (701 mg, mw 282.3, 2.5 mmol), alanine tert-butyl ester, hydrochloride salt, (454 mg, mw 181.7, 2.5 mmol) and NaBH₃CN (236 mg, mw 62.8, 3.75 mmol) were suspended in methanol (10 mL) in a 25 mL round-bottom flask and stirred at 25° C. for 60 minutes. The suspension was concentrated to dryness in vacuo and the remaining oil was resuspended in dioxane-water (1:1, 4 mL). Solid NaHCO₃ (630 mg, mw 84.0, 7.5 mmol) was added, and the suspension was cooled in an ice-bath. Fmoc-Cl (971 mg, mw 258.7, 3.75 mmol) was dissolved in dioxane (3 mL) and added to the suspension. Stirring was continued for I hour while cooling in an ice-bath and at 25° C. overnight. The pH was then adjusted to 9 by addition of saturated aqueous NaHCO₃ (6 mL). The suspension was diluted with water (20 mL) and washed with diethyl ether (2×35 mL). The aqueous layer was acidified to pH 2 with 1.5 N aqueous HCl and extracted with ethyl acetate (3×20 mL). The combined organic phases were dried over MgSO₄, filtered and concentrated to dryness in vacuo to provide an oil (905 mg, 57%).

¹H NMR (500 MHz, DMSO-d₆, 368K) δ11.1 (broad s; 1H), 7.85 (d, J=7.6; 2H), 7.66 (t, J=6.6; 2H), 7.40 (t, J=7.5; 2H), 7.31 (ddt, J=7.5, 2.8, 1.1; 2H), 6.23 (s; 2H), 4.58 (d, J=13.7; 2H), 4.44 (m; 1H), 4.40 (d, J=13.7; 2H), 4.28–4.24 (m; 2H), 4.02 (t, J=6.5; 2H), 3.75 (d, J=7.5; 1H), 3.72 (s; 6H), 3.66 (d, J=7.0; 1H), 2.29 t, J=9 7.2; 2H), 1.97 (s; 2H), 1.75 (m; 2H), 1.70 (m; 2H), 1.32 (s; 7H), 1.09 (d, J=6.7; 2H).

FABMS m/z calcd for $C_{36}H_{43}NO_9$: 633.3, found: 633.3 [M⁺.].

Example 5

N$^\alpha$-[4-(carboxylbutyloxy)-2,6-dimethoxybenzyl]-N$^\alpha$-(9-fluorenylmethoxycarbonyl)-2,2-dimethoxyethylamine 5-(4-Formyl-3,5-dimethoxyphenoxy)valeric acid (560 mg, mw 282.3, 2.0 mmol), 2,2-dimethoxyethylamine (261 μL, mw 105.1, ρ 0.97, 2.4 mmol) and molecular sieves 3 Å (100 mg) were combined in a 25 mL round-bottom flask. Methanol (10 mL) was added, and the reaction mixture was refluxed with magnetic stirring for 90 minutes. After cooling to 25° C., NaBH₃CN (189 mg, mw 62.8, 3.0 mmol) was added in two portions over 5 minutes and stirring continued for 60 minutes. The suspension was concentrated to dryness in vacuo and stored overnight at −20° C. The remaining oil was resuspended in dioxane-water (3:2, 25 mL), and solid NaHCO₃ (840 mg, mw 84.0, 10 mmol) was added. The suspension was cooled in an ice-bath. Fmoc-OSu (890 mg, mw 337.3, 2.64 mmol) was dissolved in dioxane (8 mL) with gentle heating and added from an addition funnel over 15 minutes to the suspension. Stirring was continued for 2 hours while cooling on an ice-bath and then for 2 hours at 25° C. The suspension was diluted with water (15 mL) and washed with diethyl ether (30 mL). The aqueous layer was diluted with water (50 mL) and extracted with diethyl ether (50 mL). The aqueous layer was acidified to pH 3 by addition of 0.5 N aqueous HCl and extracted with ethyl acetate (4×50 mL). The combined organic phases were dried over MgSO₄, filtered and concentrated to dryness in vacuo to an oil. The oil was stored at −20° C. overnight. The oil was then dissolved in diethyl ether (100 mL) at 25° C. and hexane was added until cloudiness occurred. Storage at −20° C. overnight resulted in the formation of crystals together with some oil. The mixture was concentrated to dryness in vacuo, and suspended in diethyl ether. After concentration to 50 mL in vacuo hexane was added until the onset of cloudiness. It was stored at −20° C. overnight after which crystals had formed (503 mg, 42%).

¹H NMR (500 MHz, DMSO-d₆, 294 K) δ12.05 (broad s; 1H), 7.85 (t, J=7.7; 2H), 7.65 (broad s; 2H), 7.39 (q, J=14.3, 7.3; 2H), 7.31 (t, J=7.5; 2H), 6.21 (broad s; 1H), 6.18 (broad s; 1H), 4.47 (m; 2H), 4.26 (t, J=~6; 2H), 3.97 (d, J=6.1; 2H), 3.67 (s; 6H), 3.21 (s; 3H), 3.04 (s; 3H), 2.28 (t, J=7.3; 2H), 1.70 (m; 2H), 1.65 (m; 2H).

FABMS m/z calcd for $C_{33}H_{39}NO_9$: 593.67, found: 593.1 [M⁺.], 592.3 [M−H⁻].

Example 6

N$^\alpha$-[2-(carboxylbutyloxy)-4,6-dimethoxybenzyl]-N$^\alpha$-(9-fluorenylmethoxycarbonyl)glycine allyl ester 5-(²-Formyl-3,5-dimethoxyphenoxy)valeric acid (2.80 g, mw 282.3, 10.0 mmol), glycine allyl ester, trifluoroacetate salt, (2.15 g, mw 229.2, 9.4 mmol; prepared as in Example 2) and NaBH₃CN (0.95 g, 62.8, 15 mmol) were suspended in methanol (45 mL) in a 50 mL round-bottom flask and stirred at 25° C. for 60 minutes. The suspension was concentrated to dryness in vacuo in a 250 mL round-bottom flask and the remaining oil was resuspended in dioxane-water (1:1, 16 mL). Solid NaHCO₃ (2.6 g, mw 84.0, 30 mmol) was added and the suspension was cooled in an ice-bath. Fmoc-Cl (2.9 g, mw 258.7, 11.0 mmol) dissolved in dioxane (approximately 4 mL) was added to the suspension and stirring continued for 1 hour while cooling in an ice-bath, and at 25° C. overnight. The suspension was diluted with water (20 mL), the pH was adjusted to 9 with saturated aqueous NaHCO₃, and then extraction was carried out with diethyl ether (2×25 mL). The aqueous layer was acidified to pH 3 by addition of 1.5 N aqueous HCl (10 mL) and extracted with ethyl acetate (3×50 mL). The combined organic phases were dried over MgSO₄, filtered and concentrated to dryness in vacuo to provide an oil (4.31 g, 76%).

$^1$H NMR (500 MHz, DMSO-$d_6$, 368 K) δ7.85 (d, J=7.6; 2H), 7.80 (d, J=7.6; 2H), 7.40 (dt, J=7.5, 1.1; 2H), 7.33 (dt, J=7.5, 1.1; 2H), 6.21 (s; 1H), 6.19 (s; 1H), 5.89 (m; 1H), 5.28 (dq, J=17.2, 3.1, 1.5; 1H), 5.19 (dq, J=10.5, 2.8, 1.4; 1H), 4.52 (dt, J=5.5, 1.4; 2H), 3.96 (t, J=6.2; 2H), 3.75 (s; 6H), 3.67 (s; 2H), 2.28 (t, J=7.1; 2H), 1.75 (dd, J=13.3, 6.6; 2H), 1.70 (dd, J=14.8, 7.9; 2H).

FABMS m/z calcd for $C_{34}H_{37}NO_9$: 603.25, found: 603.2 [M⁺.], 648.4 [M–H+2Na].

Example 7

N$^\alpha$-[4-(carboxylbutyloxy)benzyl]-N$^\alpha$-(9-fluorenylmethoxycarbonyl)leucine tert-butyl ester 4-(4-Formyl-phenoxy)butyric acid (104 mg, mw 208.2, 0.50 mmol), leucine tert-butyl ester, hydrochloride salt, (112 mg, mw 223.8, 0.50 mmol) and NaBH₃CN (47 mg, mw 62.8, 0.75 mmol) were suspended in methanol (5 mL) in a 25 mL round-bottom flask stirred at 25° C. for 7 hours. The suspension was concentrated to dryness in vacuo and the remaining oil was resuspended in dioxane-water (1:1, 4 mL), and solid NaHCO₃ (126 mg, mw 84.0, 1.5 mmol) added. The suspension was cooled in an ice-bath. Fmoc-Cl (142 mg, mw 258.7, 0.55 mmol) was dissolved in dioxane (2 mL) and added to the suspension. Stirring was continued for 1 hour while cooling in an ice-bath, and at 25° C. for 20 hours. The suspension was diluted with water (20 mL), which caused an emulsion to form. The emulsion was concentrated in vacuo at 40° C. to remove dioxane, and then extracted with hexane (2×25 mL). The phase separations were slow. The aqueous layer was acidified to pH 3 by addition of 0.5 N aqueous HCl and extracted with ethyl acetate (3×25 mL). The combined organic phases were dried over MgSO₄, filtered and concentrated to dryness in vacuo to provide an oil (64 mg, 21%).

$^1$H NMR (500 MHz, DMSO-$d_6$, 294 K) δ12.12 (broad s; 1H), 7.84 (d, J=7.3; 2H), 7.63 (t, J=7.3; 1H), 7.53 (t, J=10.1, 7.9; 1H), 7.38 (m; 2H), 7.32–7.22 (m; 2H), 7.08 (d, J=7.9), 6.85 (d, J=8.2; 1H), 6.79 (d, J=8.2; 1H), 6.70 (d, J=8.2; 1H), 4.53 (d, J=5.2; 2H), 4.24 (t, J=4.9; 1H), 4.16–4.10 (m; 1H), 3.95 (m; 1H), 3.92 (t, J=6.5; 2H), 2.35 (m; 2H), 1.90 (m; 2H), 1.51 (m; 1H), 1.26 (s, 9H), 0.68 (d, J=6.4; 1.5H), 0.62 (d, J=6.4; 1.5H), 0.49 (d, J=6.4; 1.5H), 0.44 (d, J=6.1; 1.5H).

FABMS m/z calcd for $C_{36}H_{43}NO_7$: 601.30, found: 602.3 [MH⁺].

Example 8

Coupling of N$^\alpha$-[4-(carboxylbutyloxy)-2,6-dimethoxybenzyl]-N$^\alpha$-(9-fluorenylmethoxycarbonyl)-2,2-dimethoxyethylamine, Fmoc-BAL(glycinal dimethyl acetal)-OH, to PEG-PS N$^\alpha$-[4-(carboxylbutyloxy)-2,6-dimethoxybenzyl]-N$^\alpha$-(9-fluorenylmethoxycarbonyl)-2,2-dimethoxyethylamine (214 mg, mw 593.7, 0.36 mmol), BOP (160 mg, mw 442.3, 0.36 mmol), HOBt (49 mg, mw 135.1, 0.36 mmol), were dissolved in DMF (3 mL). After 5 minutes, this solution was added to neutralized PEG-PS resin (0.18 mmol/g, 1.00 g) and reaction was carried out at 25° C. overnight. The resin was washed with DMF (5×2 mL) and CH₂Cl₂ (5×2 mL). A solution of acetic anhydride-CH₂Cl₂ (1:3, 4 mL) was added and a capping reaction was carried out at 25° C. for 1 hour. The resin was washed with CH₂Cl₂ (10×2 mL) and dried in vacuo at 25° C.

Example 9

Synthesis of model peptide aldehyde H-Ala-Leu-Ala-Lys-Leu-Gly-Gly-H, (SEQ ID NO: 1)

Manual chain assembly was carried out starting with Fmoc-BAL(glycinal dimethyl acetal)-PEG-PS resin (200 mg) prepared according to Example 8. Wash volumes were 2 mL. Side-chain protection for Lys was provided by Boc. Fmoc removal was accomplished with piperidine-DMF (1:4; 5 minutes+25 minutes), followed by washes with DMF (5×2 minutes). N-Fmoc-Gly-OH (0.30 mmol, 89 mg) was dissolved in CH₂Cl₂-DMF (5:1, 1.2 mL) and a solution of DCC (31 mg, mw 206.3, 0.15 mmol) in CH₂Cl₂ (0.5 mL) was added. After 15 minutes a white precipitate was removed by filtration and the solution added to the resin. CH₂Cl₂ was added to give a total volume of 2 mL. The remaining amino acids were coupled by in turn dissolving each N$^\alpha$-Fmoc-amino acid (0.128 mmol) in DMF (1.5 mL) with BOP (43 mg, 442.3, 0.096 mmol), HOBt (13 mg, 135.1, 0.096 mmol), and DIEA (25 μl, mw 129.3, ρ 0.74, 0.145 mmol); after 5 minutes the solution was added to the growing peptidyl-resin and reacted at 25° C. for 45 minutes. For cleavage, a portion (19 mg) of the peptidyl-resin was treated first with piperidine-DMF (1:4) to remove Fmoc, followed by washings and then TFA-H₂O (19:1) for 2 hours at 25° C. The filtrate from the cleavage reaction was collected and combined with TFA washes (3×2 mL) of the cleaved peptidyl-resin, and the resultant solution was concentrated under a stream of N₂. The crude cleaved peptide was precipitated with methyl tert-butyl ether (2 mL), washed with diethyl ether (2×10 mL), and dried to give material that showed a single major component by analytical HPLC (4.6×250 mm column). ESMS m/z calcd: 612.4; found: 613.4 [MH⁺]. The amino acid composition of the hydrolyzed (A) peptidyl-resin was: Gly, 1.00; Ala, 1.98; Leu, 1.87; Lys, 0.91; Nle, 4.14. The amino acid composition of the hydrolyzed (A) crude cleaved peptide was: Gly, 1.00; Ala, 2.06; Leu, 1.86; Lys, 0.85.

Example 10

Preparation of H-BAL(Leu-OtBu)-Ile-PEG-PS by on-resin reductive amination

Coupling of N$^\alpha$-Fmoc-Ile-OH to PEG-PS: PEG-PS (1.00 g, 0.21 mmol/g) was first treated with CH₂Cl₂ (5×0.5 minute), TFA-CH₂Cl₂ (4:6, 1 minute+20 minutes), and then washed with CH₂Cl₂ (5×0.5 minute), neutralized by DIEA-CH₂Cl₂ (1:19, 3×1 minute), and washed with CH₂Cl₂ (5×0.5 minute), DMF (5×0.5 minute). Fmoc-Ile-OH (3 equivalents), HOBt (3 equivalents, 135.1) and DIPCDI (mw 126.2, ρ 0.81, 3 equivalents) were dissolved in DIMF (2 mL) and added to the resin. The reaction was carried out at 25° C. for 2 hours, at which time the resin was negative to the Kaiser ninhydrin test. The resin was washed with DMF (5×0.5 minute) and CH₂Cl₂ (3×0.5 minute), and dried.

Coupling of 5-(4-formyl-3,5-dimethoxyphenoxy)valeric acid to H-Ile-PEG-PS: N$^\alpha$-Fmoc-Ile-PEG-PS (0.1 g, 0.21 mmol/g) was first treated with piperidine-DMF (1:4, 3×1 minutes, 2×5 minutes, 2×1 minutes) and then washed with DMF (5×0.5 minute). 5-(4-formyl-3,5-dimethoxyphenoxy) valeric acid (PALdehyde; 24 mg, mw 282.3, 4 equivalents), HATU (32 mg, mw 380.2, 4 equivalents) and DIEA (29 μL, mw 129.25, ρ 0.74, 8 equivalents) were dissolved in DMF. After 1 minute, this solution was added to the resin and the coupling was allowed to proceed at 25° C. for 2 hours, at which time the resin was negative to the Kaiser ninhydrin test. The resin was washed with DMF (5×0.5 minute), $CH_2Cl_2$ (3×0.5 minute), and dried in vacuo.

Preparation of H-BAL(Leu-O$^t$Bu)-Ile-Nle-PEG-PS by solid-phase reductive amination: Leucine tert-butyl ester, hydrochloride salt, (47 mg, mw 223.8, 10 equivalents) and $NaBH_3CN$ (13 mg, mw 62.8, 10 equivalents) dissolved in DMF (0.4 mL) were added to PALdehyde-Ile-PEG-PS (100 mg) and the reaction was allowed to proceed at 25° C. for 1 hour. The resin was then washed with DMF (5×0.5 minute), $CH_2Cl_2$ (3×0.5 minute), DMF (3×0.5 minute), piperidine-DMF (1:4, 3×1 minutes), DMF (5×0.5 minute), and $CH_2Cl_2$ (3×0.5 minute).

Example 11

Synthesis of model peptide H-Tyr-Gly-Gly-Phe-Leu-OH, Leu-enkephalin (SEQ ID NO: 2)

Manual chain assembly was carried out starting with H-BAL(Leu-OtBu)-Ile-PEG-PS resin (100 mg) prepared according to Example 10. Wash volumes were 2 mL. Side-chain protection for Tyr was provided by tBu. Fmoc removal was accomplished with piperidine-DMF (1:4; 3×1 minutes, 2×5 minutes, 2×1 minutes), followed by washes with DMF (5×0.5 minute). N$^\alpha$-Fmoc-Phe-OH (10 equivalents, mw 387.4, 81 mg) was dissolved in $CH_2Cl_2$-DMF (9:1, 0.5 mL) and DIPCDI (20 μL, mw 126.2, ρ 0.81, 6 equivalents) was added. After 5 minutes, the solution was added to the growing peptidyl-resin and the coupling was allowed to proceed at 25° C. for 2 hours. The resin was subsequently washed with $CH_2Cl_2$ (5×0.5 minute) and DMF (5×0.5 minute), and the coupling was repeated once. The remaining amino acids were coupled by in turn dissolving each N$^\alpha$-Fmoc-amino acid (5 equivalents), DIPCDI (5 equivalents) and HOBt (5 equivalents) in DMF. Amino acid composition of the hydrolyzed (B) peptidyl-resin: Tyr, 0.85; Gly, 1.69; Phe, 0.85; Leu, 0.97; Ile, 1.00; Nle, 3.04.

The completed peptidyl-resin (50 mg) was treated first with piperidine-DMF (1:4) to remove Fmoc, followed by washings with DMF (5×1 minute) and $CH_2Cl_2$ (5×1 minute), and then cleaved with TFA-$H_2O$ (19:1, 1 mL) for 1 hour at 25° C. The filtrate from the cleavage reaction was collected and combined with TFA washes (1 mL) of the cleaved peptidyl-resin, and concentrated under a stream of $N_2$ to give material that showed a single major component by analytical HPLC ($t_R$: 18.7 minutes; 4.6×250 mm Vydac column, linear gradient over 30 minutes of 0.1% TFA in $CH_3CN$ and 0.1% aqueous TFA from 1:9 to 4:6, flow rate 1.0 mL/minute, UV detection at 220 nm). The cleavage yield was 90% according to hydrolysis (B) of resin after cleavage: Tyr, 0.08, Gly, 0.17, Phe, 0.08, Leu, 0.13, Ile, 1.00, Nle, 3.05. FABMS Wmz calcd: 555.2 ; found: 556.2 [MH$^+$].

Example 12

Synthesis of Leu-enkephalin $C_8$ ester (YGGFL-OOctyl)

The same procedures as described in Examples 10 and 11 were followed, except that PEG-PS was substituted with MBHA (0.57 mmol/g, 50 mg) and leucine tert-butyl ester, hydrochloride salt with leucine octyl ester, hydrochloride salt (80 mg, mw 279.8, 10 equivalents). N$^\alpha$-Ddz-Phe-OH (110 mg, 10 equivalents), PyAOP (148 mg, mw 521.4, 10 equivalents), and DIEA (97 μL, mw 129.3, ρ 0.74, 20 equivalents) were dissolved in in $CH_2Cl_2$-DMF (9:1, 1 mL) and added to H-BAL(Leu-OOctyl)-Ile-MBHA and the reaction was carried out at 25° C. for 2 hours. The peptidyl-resin was washed with $CH_2Cl_2$ (5×0.5 minute) and the coupling repeated twice (At this point, the amino acid composition of the hydrolyzed (B) peptidyl-resin was Leu, 0.98; Phe, 1.00). Treatment with TFA-$H_2O$-$CH_2Cl_2$ (3:1:96, 6×1 minute) removed the Ddz group. Fmoc-Gly-OH (85 mg, mw 297.3, 10 equivalents), PyAOP (148 mg, 10 equivalents), and DIEA (97 μL, 20 equivalents) were dissolved in DMF (0.4 mL) and the solution added to the resin. The reaction was allowed to proceed at 25° C. for 2 hours, at which time the Kaiser ninhydrin test was negative. The remaining amino acids were coupled as in Example 11. Cleavage of the final peptide was accomplished with TFA-$H_2O$ (19:1, 1 mL) at 25° C. for 90 minutes, and was pure by HPLC (98%, $t_R$ 40.1 minutes; 4.6×250 mm Nucleosil column, linear gradient over 30 minutes of 0.1% TFA in $CH_3CN$ and 0.1% aqueous TFA from 1:9 to 4:6, 10 minutes from 4:6 to 10:0, flow rate 1.0 mL/minute, UV detection at 220 nm). The cleavage yield was 86% according to hydrolysis (B) of resin after cleavage. MALDI-TOF MS m/z calcd: 667.6 ; found: 668.9 [MH$^+$], 692.6 [MNa$^+$]. Amino acid composition of the hydrolyzed (B) final peptidyl-resin: Tyr, 0.97; Gly, 1.96; Phe, 0.98; Leu, 1.06; Ile, 1.00.

Example 13

Preparation of H-BAL(Ala-OAl)-Ile-MBHA by on-resin reductive amination

Preparation of o,p-PALdehyde-Ile-MBHA: N$^\alpha$-Fmoc-Ile-MBHA (0.57 mmol/g, 50 mg) was first treated with piperidine-DMF (1:4, 3×1 minute+2×5 minutes+2×1 minute) and then washed with DMF (5×0.5 minute). A mixture of 5-(2-formyl-3,5-dimethoxyphenoxy)butyric acid and 5-(4-formyl-3,5-dimethoxyphenoxy)butyric acid (o,p-PALdehyde; 31 mg, mw 268.3, 4 equivalents), HATU (43 mg, mw 380.2, 4 equivalents), and DIEA (39 μL, mw 129.25, ρ 0.74, 8 equivalents) were dissolved in DMF (0.4 mL). After 1 minute the solution was added to the resin and the reaction allowed to proceed at 25° C. for 2 hours, at which time the resin was negative to the Kaiser ninhydrin test. The resin was washed with DMF (5×0.5 minute), $CH_2Cl_2$ (3×0.5 minute), and dried in vacuo.

Preparation of H-BAL(Ala-OAl)-Ile-MBHA by solid-phase reductive amination: H-Ala-OAl, hydrochloride salt (47 mg, mw 243.2, 10 equivalents) and $NaBH_3CN$ (18 mg, mw 62.8, 10 equivalents) were dissolved in DMF (0.5 mL) and added to o,p-PALdehyde-Ile-MBHA (50 mg) and the reaction was allowed to proceed at 25° C. for 18 hours. The resin was then washed with DMF (5×0.5 minute), $CH_2Cl_2$ (3×0.5 minute), DMF (3×0.5 minute), piperidine-DMF (1:4, 3×1 minute), DMF (5×0.5 minute), $CH_2Cl_2$ (3×0.5 minute), and dried in vacuo.

Example 14

Synthesis of model linear peptide Fmoc-Arg-DPhe-Pro-Glu-Asp-Asn-Tyr-Glu-Ala-Ala-OAl Manual chain assembly was carried out starting with H-BAL(Ala-OAl)-Ile-MBHA resin (50 mg) prepared according to Example 13. Wash volumes were 2 mL. Side-chain protection was provided by Pmc (Arg), Trt (Asn), and tBu (Asp, Glu, Tyr). Fmoc removal was accomplished with piperidine-DMF (1:4; 3×1 minute+2×5 minutes+2×1 minute), followed by washes with DVIF (5×0.5 minute). $N^{\alpha}$-Trt-Ala-OH (94 mg, mw 331.4, 10 equivalents), PyAOP (148 mg, mw 521.4, 10 equivalents), and DIEA (97 µL, mw 129.3, ρ 0.74, 20 equivalents) were dissolved in DMF-$CH_2Cl_2$ (1:9), added to H-BAL(Ala-OAl)-Ile-MBHA (50 mg) and the reaction was carried out at 25° C. for 2 hours. The peptidyl-resin was washed with $CH_2Cl_2$ (5×0.5 minute), DMF (5×0.5 minute) and the coupling repeated. Treatment with TFA-$H_2O$-$CH_2Cl_2$ (1:1:98, 5×1 minute) removed the Trt group. Fmoc-Glu(OtBu)-OH (121 mg, mw 425.5, 10 equivalents), PyAOP (148 mg, 10 equivalents) and DIEA (97 µL, 20 equiv) were dissolved in DMF (0.4 mL) and the solution added to the resin. The reaction was allowed to proceed at 25° C. for 2 hours, at which time the Kaiser ninhydrin test was negative. The remaining seven amino acid residues were consecutively coupled to the resin using Fmoc-AA-OH (5 equivalents), PyAOP (5 equivalents) and DIEA (10 equivalents) in DMF. Amino acid composition of the hydrolyzed (B) peptidyl-resin was: Ala, 2.35; Arg, 0.90; Phe, 1.03; Pro, 0.87; Glu, 1.92; Asp, 1.93; Tyr, 1.01. The synthesis yield was 88% with respect to "internal reference" amino acid Ile. The final protected peptide was cleaved from the resin by treatment with TFA-$Et_3SiH$-$H_2O$ (92:5:3) at 25° C. for 2 hours and was pure by HPLC (>65%, $t_R$ 17.8 minutes; 4.6×250 mm Nucleosil column, linear gradient over 30 minutes of 0.1% TFA in $CH_3CN$ and 0.1% aqueous TFA from 1:9 to 10:0, flow rate 1.0 mL/minute, UV detection at 220 nm). MALDI-TOF MS: m/z calcd 1478.4; found 1474.8 [MH$^+$].

Example 15

Cyclization of the peptide Fmoc-Arg-DPhe-Pro-Glu-Asp-Asn-Tyr-Glu-Ala-Ala-OAl

The Fmoc and Al protected peptidyl-resin (10 mg) was washed with DMF (5×0.5 minute) followed by Pd(PPh$_3$)$_4$ (mw 1155.58, 5 equivalents) in DMSO-THF-0.5 N HCl-morpholine (2:2:1:0.1, 1.53 mL) at 25° C. for 3 hours under argon to cleave the C-terminal Al ester. The peptidyl-resin was washed with THF (3×2 minutes), DMF (3×2 minutes), $CH_2Cl_2$ (3×2 minutes), DIEA-$CH_2Cl_2$ (1:19, 3×2 minutes), $CH_2Cl_2$ (3×2 minutes), diethyldithiocarbamic acid, sodium salt (0.03 M in DMF, 3×15 minutes), DMF (5×2 minutes), $CH_2Cl_2$ (3×2 minutes) and DMF (3×1 minute). Fmoc was removed with piperidine-DMF (1:4, 3×1 minute+2×5 minutes+2×1 minute) and the peptide cyclized on resin in $CH_2Cl_2$ by treatment with PyAOP (5 equivalents), HOAt (5 equivalents) and DIEA (10 equivalents) for 2 hours, at which time the resin was negative to the Kaiser ninhydrin test. The peptide was cleaved from the resin by treatment with TFA-$Et_3SiH$-$H_2O$ (92:5:3) at 25° C. for 3 hours and by HPLC showed a single major component ($t_R$ 21.0 minutes; 4.6×250 mm Nucleosil column, linear gradient over 30 minutes of 0.1% TFA in $CH_3CN$ and 0.1% aqueous TFA from 1:9 to 4:6, flow rate 1.0 mL/minute, UV detection at 220 nm, 64% purity). MALDI-TOF MS: m/z calcd 1193.6; found 1193.7 [MH$^{30}$].

Example 16

Ethyl 5-(4-formyl-3-hydroxyphenoxy)valerate

Potassium tert-butoxide (2.1 g, mw 112.2, 19 mmol) was added to a solution of 2,4-dihydroxybenzaldehyde (2.5 g, mw 138.1, 18 mmol) in dry DMF (18 mL) and the resultant suspension stirred under $N_2$ at 25° C. for 5 minutes. Ethyl 5-bromovalerate (2.9 mL, mw 209. 1, ρ 1.32, 19 mmol) dissolved in dry DMF (18 mL) was added, and the reaction heated at 110° C. for 5 hours, following which DMF was removed at 60° C. and 2 mm Hg. The residue was taken up in ethyl acetate (100 mL), washed with water (50 mL), and extracted with 1 N aqueous NaOH (50 mL). The ethyl acetate phase was washed with brine (2×50 mL), dried over $Na_2SO_4$, and concentrated to yield 1.69 g of an amber colored solid. The NaOH phase was acidified to pH 3 with 6 N aqueous HCl and extracted with ethyl acetate (3×25 mL). The organic extract was washed with brine (2×50 mL), dried over $Na_2SO_4$, filtered and concentrated to yield 2.54 g of a very dark solid. TLC ($CHCl_3$-methanol, 99:1) indicated that both solids were composed of the same two products ($R_f$ 0.37, 0.60), thus they were combined and purified by flash chromatography on silica ($CHCl_3$-methanol, 99:1) to yield 1.69 g (35%) of title product ($R_f$ 0.37) and 0.44 g of the dialkylated product, diethyl 6-formyl-1,3-phenylenebis(5-oxyvalerate). Both compounds were NMR and TLC pure white solids. For the title product, $^1$H NMR (300 MHz, $CDCl_3$, 294 K) δ11.46 (s; OH), 9.70 (s; CHO), 7.41 (d, J=8.6; 1H), 6.51 (dd, J=2.2, 8.6; 1H), 6.39 (d, J=2.2; 1H), 4.13 (q, J=7.1; 2H), 4.02 (t, J=5.7; 2H), 2.37 (t, J=6.9; 2H), 1.82 (m; 4H), 1.25 (t, J=7.1; 3H).

FABMS m/z calcd for $C_{14}H_{18}O_5$: 266.3, found: 267.1 [MH$^{30}$].

For the dialkylated product, $^1$H NMR (300 MHz, $CDCl_3$, 294 K) δ10.29 (s), 7.76 (d, J=8.7; 1H), 6.48 (dd, J=1.9, 8.7; 1H), 6.38 (d, J=1.9; 1H), 4.10 (q, J=7.1; 4H), 4.01 (overlapping t; 4H), 2.37 (overlapping t; 4H), 1.80 (m; 8H), 1.23 (t, J=7.1; 6H).

FABMS m/z calcd for $C_{21}H_{30}O_7$: 394.5, found: 395.2 [MH$^+$].

Example 17

5-(4-Formyl-3-hydroxyphenoxy)valeric acid

2 N aqueous NaOH (10 mL) was added to ethyl 5-(4-formyl-3-hydroxyphenoxy)valerate (1.5 g, mw 266.3, 5.8 mmol; prepared as in Example 16) dissolved in methanol (20 mL) and the solution stirred at 25° C. for 1 hour, at which point TLC ($CHCl_3$-methanol, 99:1) indicated the reaction was complete. Methanol was removed under reduced pressure and the reaction diluted with water (50 mL), washed with ethyl acetate (3×15 mL, discarded), acidified to pH 4 with 6 N aqueous HCl, and extracted with ethyl acetate (4×25 mL). The combined organic extracts were washed with brine (2×50 mL), dried over $Na_2SO_4$, filtered, and concentrated to yield 1.35 g (98%) of a white solid. A portion of the solid was purified by flash chromatography on silica ($CHCl_3$-methanol, 45:1) and recrystallized from boiling ethyl acetate-hexane to provide NMR and TLC ($R_f$ origin) pure title product; $^1$H NMR (500 MHz, $CDCl_3$, 294 K) δ11.47 (s), 9.71 (s), 7.42 (d, J=8.6; 1H), 6.53 (dd, J=2.3, 8.6; 1H), 6.41 (d, J=2.3; 1H), 4.04 (t, J=5.8; 2H), 2.46 (t, J=7.0; 2H), 1.86 (m; 4H).

Example 18

Ethyl 5-(4-formyl-2,6-dimethylphenoxy)valerate

Potassium tert-butoxide (2.1 g, mw 112.2, 18 mmol) was added to a solution of 4-formyl-2,6-dimethylphenol (2.5 g, mw 150.2, 17 mmol) in dry DMF (15 mL) and the resultant suspension stirred under $N_2$ at 25° C. for 5 minutes. Ethyl 5-bromovalerate (2.8 mL, mw 209.1, ρ 1.32, 18 mmol) dissolved in dry DMF (15 mL) was added, and the reaction heated at 110° C. for 5 hours, following which DMF was removed at 60° C. and 2 mm Hg. The residue was taken up in ethyl acetate (125 mL), washed with water (25 mL), 1 N aqueous NaOH (25 mL), and brine (75 mL), dried over $Na_2SO_4$, filtered, and concentrated to yield 4.47 g (97%) of NMR and TLC ($R_f$ 0.58, $CHCl_3$-methanol, 99:1) pure title product as an amber oil.

$^1$H NMR (300 MHz, $CDCl_3$, 294 K) δ9.87 (s), 7.55 (s; 2H), 4.15 (q, J=7.1; 2H), 3.83 (t, J=6.0; 2H), 2.41 (t, J=7.0; 2H), 2.33 (s; 6H), 1.87 (m; 4H), 1.26 (t, J=17.1; 3H).

Example 19

5-(4-Formyl-2,6-dimethylphenoxy)valeric Acid

2 N aqueous NaOH (30 mL) was added to ethyl 5-(4-formyl-2,6-dimethylphenoxy)valerate (4.0 g, mw 278.4, 14 mmol; prepared as in Example 18) dissolved in methanol (40 mL) and that the solution stirred at 25° C. for 1 hour, at which point TLC ($CHCl_3$-methanol, 99:1) indicated the reaction was complete. Methanol was removed under reduced pressure and the reaction diluted with water (150 mL), washed with ethyl acetate (2×25 mL, discarded), acidified to pH 4 with 6 N aqueous HCl, and extracted with ethyl acetate (3×30 mL). The organic extract was washed with brine (2×75 mL), dried over $Na_2SO_4$, filtered and concentrated to yield 3.57 g (99%) of an amber oil. A portion of the oil was purified by flash chromatography on silica ($CHCl_3$-methanol, 45:1) to provide NMR and TLC ($R_f$ origin) pure title product:

$^1$H NMR (500 MHz, $CDCl_3$, 294 K) δ9.87 (s; CHO), 7.55 (s; 2H), 3.84 (t, J=5.9; 2H), 2.49 (t, J=7.0; 2H), 2.33 (s; 6H), 1.90 (m; 4H).

FABMS m/z calcd: 250.3 for $C_{14}H_{18}O_4$, found: 251.1 [MH$^+$].

Example 20

5-(4-(N-Fmoc-N-methyl)aminomethyl-3,5-dimethoxyphenoxy)valeric acid

Methylamine (13.3 mL of a 2 M solution in MeOH, 26.6 mmol) was added to a solution of 5-(4-formyl-3,5-dimethoxyphenoxy)valeric acid (5.0 g, 17.7 mmol) in MeOH (150 mL) under $N_2$ at 0° C. The reaction was allowed to warm to 25° C., stirred at reflux for 2 hours, and then cooled to 25° C. NaBH$_3$CN (1.67 g, 26.6 mmol) was added, and the reaction stirred for 1 hour at 25° C. Solvent was removed under reduced pressure, and the residue was taken up in dioxane-10% $Na_2CO_3$ (1:1, 170 mL) and cooled to 0° C. Fmoc-OSu (6.6 g, 19.5 mmol) dissolved in minimal dioxane (approximately 10 mL) was added slowly, and the reaction stirred for 15 hours at 25° C. The reaction was washed with ether (3×75 mL), diluted with water (150 mL), and carefully acidified to pH 3.0 with 6 N HCl under cooling. The aqueous mixture was extracted with EtOAc (4×50 mL), and the combined organic extracts were washed with brine (2×100 mL), dried ($Na_2SO_4$), concentrated, and dried in vacuo to yield 6.78 g (74%) of the title product as an off-white solid. The product was crystallized from ether-hexane (65% recovery); mp 126.5–127.5° C.

$^1$H NMR (300 MHz, $CDCl_3$, 294μ) δ7.76 (d, J=7.3 Hz, 2H), 7.71 (d, J=7.3 Hz, 1H), 7.61 (d, J=7.3 Hz, 1H), 7.39 (dd, J=7.3, 7.3 Hz, 2H), 7.30 (dd, J=7.3, 7.3 Hz, 2H), 6.12 (s, 2H), 4.66 (s, 1H), 4.59 (s, 1H), 4.39 (m, 2H), 4.30 (m, 1H), 4.00 (t, J=5.5 Hz, 2H), 3.77 (s, 3H), 3.74 (s, 3H), 2.73 (s, 3H), 2.47 (t, J=6.8 Hz, 2H), 1.86 (m, 4H).

FABMS, calcd for $C_{30}H_{33}NO_7$: 519.6, found: m/z 520.2 [MH$^+$].

Elemental analysis: calcd for $C_{30}H_{33}NO_7$, mw 519.60: C, 69.35; H, 6.40; N, 2.70; found: C, 69.20; H, 6.42; N, 2.72.

Example 21

5-(4-(N-Fmoc-N-ethyl)aminomethyl-3,5-dimethoxyphenoxy)valeric acid

The same procedures as in Example 20 were followed, except that methylamine was substituted with ethylamine (2 M in MeOH, 18 mmol scale, 61% yield); mp 114.8–115.3° C.

$^1$H NMR (300 MHz, $CDCl_3$, 294μ) δ7.76 (d, J=7.1 Hz, 2H), 7.71 (d, J=7.1 Hz, 1H), 7.60 (d, J=7.1 Hz, 1H), 7.39 (dd, J=7.1, 7.1 Hz, 2H), 7.29 (dd, J=7.1, 7.1 Hz, 2H), 6.11 (s, 2H), 4.67 (s, 1H), 4.57 (s, 1H), 4.41 (m, 2H), 4.30 (m, 1H), 3.99 (m, 2H), 3.76 (s, 3H), 3.74 (s, 3H), 3.16 (q, J=6.7Hz, 1H), 3.07 (q, J=6.7 Hz, 1H), 2.47 (m, 2H), 1.86 (m, 4H), 1.01 (t, J=6.7, 1.5H), 0.90 (t, J=6.7 Hz, 1.5H).

FABMS, calcd for $C_{31}H_{35}NO_7$: 533.6, found: m/z 534.3 [MH$^+$].

Elemental analysis: calcd for $C_{31}H_{35}NO_7$, mw 533.63: C, 69.77; H, 6.61; N, 2.63; found: C, 69.69; H, 6.60; N, 2.65.

Example 22

5-(4-(N-Fmoc-N-phenethyl)aminomethyl-3,5-dimethoxyphenoxy)valeric acid

The same procedures as in Example 20 were followed, except that methylamine was substituted with phenethylamine (18 mmol scale, 85% yield); mp 141.5–144.5° C.

1H NMR (300 MHz, $CDCl_3$, 294μ) δ7.8–7.1 (m, 13H), 6.11 (s, 1H), 6.04 (s, 1H), 4.66 (s, 1H), 4.57 (s, 1H), 4.50 (d, J=6.7 Hz, 1H), 4.42 (d, J=6.7 Hz, 1H), 4.29 (t, J=6.7 Hz, 0.5H), 4.22 (t, J=6.7 Hz, 0.5H), 3.98 (m, 2H), 3.74 (s, 6H), 3.29 (t, J=6.7 Hz, 1H), 3.10 (t, J=6.7 Hz, 1H), 2.72 (t, J=6.7 Hz, 1H), 2.45 (m, 3H), 1.84 (m, 4H).

FABMS, calcd for $C_{37}H_{39}NO_7$: 609.7, found: m/z 610.3 [MH$^+$].

Elemental analysis: calcd for $C_{37}H_{39}NO_7$, mw 609.73: C, 72.89; H, 6.45; N, 2.30; found: C, 71.35; H, 6.39; N, 2.59.

Example 23

5-(4-(N-4-nitrophenyl)aminomethyl-3,5-dimethoxyphenoxy)valeric acid

A solution of aldehyde 5-(4-formyl-3,5-dimethoxyphenoxy)valeric acid (2.5 g, 8.86 mmol), 4-nitroaniline (1.8 g, 13.3 mmol), and NaBH$_3$CN (0.83 g, 13.3 mmol) was refluxed in MeOH (100 mL) for 15 hours under $N_2$. The reaction was allowed to cool to 25° C., and solvent was removed under reduced pressure. The residue was dissolved in 1 N aqueous NaOH (200 mL), washed with EtOAc (2×100 mL), and the organic wash was back-extracted with 1 N aqueous NaOH (100 mL). The combined basic fractions were acidified to pH 4 with 6 N HCl and extracted with EtOAc (4×50 mL). The organic extract was washed with brine (100 mL), dried ($Na_2SO_4$), concentrated, and dried in vacuo to yield 3.2 g (89%) of crude title product as a yellow solid; mp 138.5–139.5° C.; $^1$H NMR ($CDCl_3$) δ8.05 (d, J=9.2, 2H), 6.63 (d, J=9.2 Hz, 2H), 6.12 (s, 2H), 4.37 (s, 2H), 3.97 (broad t, 2H), 3.84 (s, 6H), 2.45 (broad t, 2H), 1.84 (m, 4H).

FABMS, calcd for $C_{20}H_{24}N_2O_7$: 404.4, found: m/z 405.1 [MH$^+$].

Elemental analysis: calcd for $C_{20}H_{24}N_2O_7$, mw 404.42: C, 59.40; H, 5.98; N, 6.93; found: C, 59.20; H, 5.86; N, 6.76.

Example 24

Preparation of Fmoc(R)-PAL-PEG-PS resins

Fmoc-(R)PAL-OH (prepared as in Examples 20–22, 3 equivalents), BOP (3 equivalents), HOBt (3 equiv), N-methyl morpholine (6 equivalents), and PEG-PS (0.18 mmol/g, 1 equivalents) were combined in DMF and reacted for 15 hours at 25° C., at which time the resins were all negative to the Kaiser ninhydrin test; final loadings: 0.16 mmol/g, based on UV quantification of released Fmoc.

Example 25

Synthesis of Des-Gly[10], methylamide[9]-LHRH (pGlu-His-Trp-Ser-Tyr-Gly-Leu-Arg-Pro-NHMe), (SEQ ID NO: 3)

Fmoc(Me)-PAL-PEG-PS resin (prepared as in Example 24; 150 mg, 0.024 mmol) was placed in a manually operated low-pressure continuous-flow synthesizer with a moving piston. The peptide was assembled using the same procedure as in Example 10, except that the couplings were monitored visually using bromophenol blue. Fmoc deprotection was accomplished with piperidine-DMF (1:4, 2×10 minutes) and was monitored based on UV absorbance. The final peptidyl-resin was washed with DMF and MeOH, and dried in a stream of $N_2$ (yield: 165 mg). A portion (72 mg) was cleaved and deprotected with TFA-thioanisole-phenol-1,2-ethanedithiol (87:5:5:3, 0.5 mL) for 90 minutes at 25° C. The resin was removed by filtration and washed with TFA (2×0.5 mL) and $CH_2Cl_2$ (2×0.5 mL). The combined filtrate and washings were concentrated, and the residue washed twice with diethyl ether. The crude peptide was taken up in 10% aqueous HOAc for final deprotection of Trp, and lyophilized (yield: 14 mg). Amino acid composition of cleaved peptide: Glu, 1.00; His, 0.92; Ser, 0.94; Tyr, 0.96; Gly, 1.07; Leu, 1.02; Arg, 1.08; Pro, 1.01. FABMS, calcd: 1139.4, found: m/z 1140.1 [MH+].

Example 26

Synthesis of Des-Gly[10], ethylamide[9]-LHRH (pGlu-His-Trp-Ser-Tyr-Gly-Leu-Ar g-Pro-NHEt), (SEQ ID NO: 4)

The same procedures as described in Example 25 were followed except that Fmoc(Me)-PAL-PEG-PS resin was substituted with Fmoc(Et)-PAL-PEG-PS resin (prepared as in Example 24; 500 mg, 0.09 mmol; yield: 580 mg). Peptidyl-resin (270 mg) was then cleaved and deprotected to give the free peptide (yield: 49 mg). Amino acid composition of cleaved peptide: Glu, 0.97; His, 0.94; Ser, 1.09; Tyr, 0.95; Gly, 1.07; Leu, 0.98; Arg, 1.08; Pro, 0.92. FABMS, calcd: 1153.4, found: m/z 1154.5 [MH+].

Abbreviations

Abbreviations used for amino acids and the designations of peptides follow the rules of the IUPAC-IUB Commission of Biochemical Nomenclature in *J. Biol. Chem.* 1972, 247, 977–983. The following additional abbreviations are used: Ac, acetyl; Al, allyl; Boc, tert.-butyloxycarbonyl; BOP, benzotriazolyl-N-oxytris(dimethylamino)phosphonium hexafluorophosphate; DIEA, N,N-diisopropylethylamine; DIPCDI, N,N'-diisopropylcarbodiimide; DMF, N,N-dimethylformamide; ESMS, electrospray mass spectrometry; Fmoc-OSu, N-(9-fluorenylmethoxycarbonyloxy) succinimide; Fmoc-Cl, 9-fluorenylmethyl chloroformate; HATU, N-[(dimethylamino)-1H-1,2,3-triazolo[4,5-b]pyridin-1-yl methylene]-N-methylmethanaminium hexafluorophosphate N-oxide; HPLC, high-performance liquid chromatography; HOBt, 1-hydroxybenzotriazole; FABMS, fast atom bombardment mass spectrometry; Fmoc, 9-fluorenylmethoxycarbonyl; MALDI-TOF, matrix assisted laser desorption/ionization time-of-flight mass spectrometry; MBHA, methylbenzhydrylamine (resin); PEG-PS, polyethylene glycol-polystyrene graft support; Pfp, pentafluorophenyl; PyAOP, 7-azabenzotriazol-1-yl-oxytris (pyrrolidino)phosphonium hexafluorophosphate; SPPS, solid-phase peptide synthesis; PALdehyde, 5-(4-formyl-3,5-dimethoxyphenoxy)valeric acid; o,p-PALdehyde, mixture of 5-(4-formyl-3,5-dimethoxyphenoxy)butyric acid and 5-(2-formyl-3,5-dimethoxyphenoxy)butyric acid; TFA, trifluoroacetic acid; Trt, trityl. Aloc, allyloxycarbonyl; Ddz, 2-(3,5-dimethoxyphenyl)isopropoxycarbonyl; Npys, 3-nitro-2-pyridinesulfenyl; Nvoc, 6-nitroveratryloxycarbonyl; Bpoc, biphenylisopropoxycarbonyl; Teoc, 2-(trimethylsilyl) ethoxycarbonyl; SES, β-trimethylsilylethane sulfonyl; t-Bu, tert-butyl; Pmc, 2,2,5,7,8-pentamethylchroman-6-sulfonyl; HOAt, 3-hydroxy-3H-1,2,3-triazolo[4,5,b]pyridine. Amino acid symbols denote the L-configuration unless stated otherwise. All solvent ratios are volume/volume unless stated otherwise.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An aldehyde-functionalized support material having the following formula (Formula III):

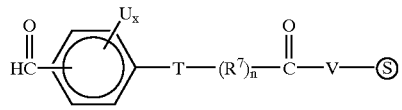

wherein:
(a) Ⓢ represents a support material;
(b) V is NH, S or O;
(c) $R^7$ is an alkylene group, an arylene group, or an oxyalkylene group;
(d) T is O, NH, NHC(O)$R^4$, or S, wherein $R^4$ is an alkylene group, an arylene group, or an aralkylene group;
(e) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups call be joined to form a ring;
(f) x=0–4; and
(g) n=1–18, with the proviso that the compound with V=NH, $R^7$=methylene, n=1, T=oxygen, x=0 and the aldehyde group para to T is excluded.

2. The aldehyde-functionalized support material of claim 1 wherein $R^7$ is an alkylene group and n=1–4.

3. A kit for synthesizing an organic compound comprising:
(a) an aldehyde-functionalized support material having the following formula (Formula III):

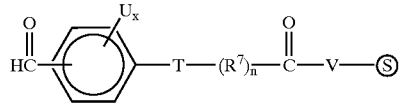

wherein:
(i) Ⓢ represents a support material;
(ii) V is NH, S or O;
(iii) $R^7$ is an alkylene group, an arylene group, or an oxyalkylene group;
(iv) T is O, NH, NHC(O)$R^4$, or S, wherein $R^4$ is an alkylene group, an arylene group, or an aralkylene group;
(v) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
(vi) x=0–4; and
(vii) n=1–18, with the proviso that the compound with V=NH, $R^7$=methylene, n=1, T=oxygen, x=0, and the aldehyde group para to T is excluded; and
(b) instructions for preparing an organic compound on the aldehyde-functionalized support material.

4. An aldehyde-functionalized solid support material having the following formula (Formula III):

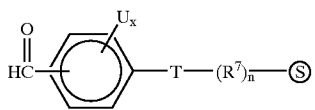

wherein:
(i) Ⓢ represents a solid support material;
(ii) $R^7$ is an alkylene group, an arylene group, or an oxyalkylene group;
(ii) T is O, NH, NHC(O)$R^4$, or S, wherein $R^4$ is an alkylene group, an arylene group, or an aralkylene group;
(iv) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
(v) x=0–4, and
(vi) n=1–18, with the proviso that the compound with $R^7$=methylene, n=1, T=oxygen, x=0, and the aldehyde group para to T is excluded.

5. The aldehyde-functionalized support material of claim 4 wherein $R^7$ is an alkylene group and n=1–4.

6. A kit for synthesizing an organic compound comprising:
(a) an) aldehyde-functionalized solid support material having the following formula (Formula III):

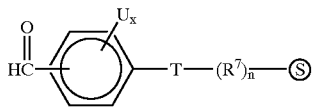

wherein:
(i) Ⓢ represents a solid support material;
(ii) $R^7$ is an alkylene group, an arylene group, or an oxyalkylene group;
(iii) T is O, NH, NHC(O)$R^4$, or S, wherein $R^4$ is an alkylene group, an arylene group, or an aralkylene group;
(iv) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
(v) x=0–4; and
(vi) n=1–18, with the proviso that the compound with $R^7$=methylene, n=1, T=oxygen, x=0, and the aldehyde group para to T is excluded; and
(b) instructions for preparing an organic compound on the aldehyde-functionalized support material.

7. An aldehyde-functionalized support material having the following formula (Formula III):

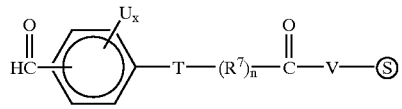

wherein:
 (a) Ⓢ represents a support material;
 (b) V is S or O;
 (c) $R^7$ is an alkylene group, an arylene group, or an oxyalkylene group;
 (d) T is O, NH, NHC(O)$R^4$, or S, wherein $R^4$ is an alkylene group, an arylene group, or an aralkylene group;
 (e) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
 (f) x=0–4; and
 (g) n=1–18.

8. The aldehyde-functionalized support material of claim 7 wherein $R^7$ is an alkylene group and n=1–4.

9. An aldehyde-functionalized support material having the following formula (Formula III):

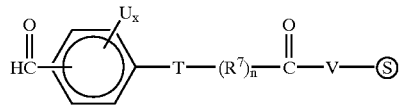

wherein:
 (a) Ⓢ represents a support material;
 (b) V is NH, S or O;
 (c) $R^7$ is an alkylene group, an arylene group, or an oxyalkylene group;
 (d) T is O, NH, NHC(O)$R^4$, or S, wherein $R^4$ is an alkylene group, an arylene group, or an aralkylene group;
 (e) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
 (f) x=1–4; and
 (g) n=1–18.

10. The aldehyde-functionalized support material of claim 9 wherein $R^7$ is an alkylene group and n=1–4.

11. A kit for synthesizing an organic compound comprising:
 (a) an aldehyde-functionalized support material having the following formula (Formula III):

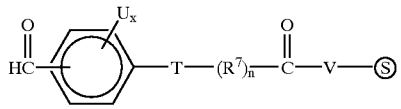

wherein:
 (i) Ⓢ represents a support material;
 (ii) V is NH, S or O;
 (iii) $R^7$ is an alkylene group, an arylene group, or an oxyalkylene group;
 (iv) T is O, NH, NHC(O)$R^4$, or S, wherein $R^4$ is an alkylene group, an arylene group, or an aralkylene group;
 (v) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
 (vi) x=1–4, and
 (vii) n=1–18; and
 (b) instructions for preparing an organic compound on the aldehyde-functionalized support material.

12. An aldehyde-functionalized solid support material having the following formula (Formula III):

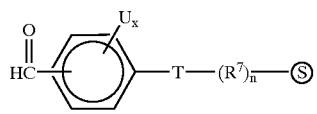

wherein:
 (i) Ⓢ represents a solid support material;
 (ii) $R^7$ is an alkylene group, an arylene group, or an oxyalkylene group;
 (iii) T is O, NH, NHC(O)$R^4$, or S, wherein $R^4$ is an alkylene group, an arylene group, or an aralkylene group;
 (iv) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
 (v) x=1–4; and
 (vi) n=1–18.

13. The aldehyde-functionalized support material of claim 12 wherein $R^7$ is an alkylene group and n=1–4.

14. A kit for synthesizing an organic compound comprising:
 (a) an aldehyde-functionalized solid support material having the following formula (Formula III):

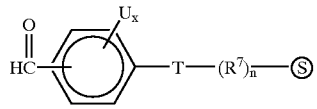

wherein:
 (i) Ⓢ represents a solid support material;
 (ii) $R^7$ is an alkylene group, an arylene group, or an oxyalkylene group;

(iii) T is O, NH, NHC(O)R$^4$, or S, wherein R$^4$ is an alkylene group, an arylene group, or an aralkylene group;
(iv) each U is independently selected from the group consisting of an alkyl group, an alkoxy group, an aryl group, an alkoxyaryl group, an aralkyl group, an aralkoxy group, an alkylthio group, an arylthio group, an alkylamido group, an alkylsulfinyl group, a halogeno group, and a nitro group, wherein any two U groups can be joined to form a ring;
(v) x=1–4; and
(vi) n=1–18; and
(b) instructions for preparing an organic compound on the aldehyde-functionalized support material.

* * * * *

UNITED STATES PATENT AND TRADEMARK OFFICE
CERTIFICATE OF CORRECTION

PATENT NO. : 6,566,494 B1
DATED : May 20, 2003
INVENTOR(S) : Knud J. Jensen et al.

It is certified that error appears in the above-identified patent and that said Letters Patent is hereby corrected as shown below:

<u>Title page,</u>
Item [75], Inventors, delete "Micheal" and insert -- Michael --

<u>Column 1,</u>
Line 60, delete "a-carboxyl" and insert -- α-carboxyl --

<u>Column 5,</u>
Line 18, delete "a-carboxyl" and insert -- α-carboxyl --

<u>Column 8,</u>
Line 63, delete "$R^1$" and insert -- $R^7$ --

<u>Column 12,</u>
Lines 66-67, delete "vaca-tion" and insert -- vacuo --

<u>Column 14,</u>
Line 66, delete "5-($^2$" and insert -- 5-(2 --

<u>Column 16,</u>
Line 61, delete "DIMF" and insert -- DMF --
Line 22, delete "N-Fmoc-Gly-OH" and insert -- $N^\alpha$-Fmoc-Gly-OH --

<u>Column 17,</u>
Line 60, delete "W" before "mz"

<u>Column 19,</u>
Line 5, delete "DVIF" and insert -- DMF --
Line 61, delete "[$MH^{30}$]" and insert -- [$MH^+$] --

UNITED STATES PATENT AND TRADEMARK OFFICE
CERTIFICATE OF CORRECTION

PATENT NO. : 6,566,494 B1
DATED : May 20, 2003
INVENTOR(S) : Knud J. Jensen et al.

It is certified that error appears in the above-identified patent and that said Letters Patent is hereby corrected as shown below:

Column 20,
Line 28, delete "[MH$^{30}$]" and insert -- [MH$^{+}$] --

Column 22,
Line 34, delete "1H" and insert -- $^{1}$H --

Signed and Sealed this

Twenty-third Day of September, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:model peptide aldehyde

```
<221> NAME/KEY: SITE
<222> LOCATION: (7)
<223> OTHER INFORMATION: Gly-H (aldehyde)

<400> SEQUENCE: 1

Ala Leu Ala Lys Leu Gly Xaa
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:model
      peptide
<221> NAME/KEY: SITE
<222> LOCATION: (5)
<223> OTHER INFORMATION: Leu-OH
<221> NAME/KEY: SITE
<222> LOCATION: (6)
<223> OTHER INFORMATION: Leu-enkephalin

<400> SEQUENCE: 2

Tyr Gly Gly Phe Xaa Xaa
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:Des-Gly10,
      methylamide9-LHRH
<221> NAME/KEY: SITE
<222> LOCATION: (1)
<223> OTHER INFORMATION: pGlu
<221> NAME/KEY: SITE
<222> LOCATION: (9)
<223> OTHER INFORMATION: Pro-NH-Me

<400> SEQUENCE: 3

Xaa His Trp Ser Tyr Gly Leu Arg Xaa
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:Des-Gly10,
      ethylamide9-LHRH
<221> NAME/KEY: SITE
<222> LOCATION: (1)
<223> OTHER INFORMATION: pGlu
<221> NAME/KEY: SITE
<222> LOCATION: (9)
<223> OTHER INFORMATION: Pro-NHEt

<400> SEQUENCE: 4

Xaa His Trp Ser Tyr Gly Leu Arg Xaa
 1               5
```